United States Patent
Han et al.

(10) Patent No.: US 10,822,355 B2
(45) Date of Patent: Nov. 3, 2020

(54) ULTRALOW-POWER NEAR INFRARED LAMP LIGHT OPERABLE TARGETED ORGANIC NANOPARTICLE PHOTODYNAMIC THERAPY

(71) Applicant: University of Massachusetts, Boston, MA (US)

(72) Inventors: Gang Han, Shrewsbury, MA (US); Ling Huang, Worcester, MA (US)

(73) Assignee: University of Massachusetts, Boston, MA (US)

(*) Notice: Subject to any disclaimer, the term of this patent is extended or adjusted under 35 U.S.C. 154(b) by 0 days.

(21) Appl. No.: 16/338,486

(22) PCT Filed: Oct. 5, 2017

(86) PCT No.: PCT/US2017/055243
§ 371 (c)(1),
(2) Date: Mar. 31, 2019

(87) PCT Pub. No.: WO2018/071256
PCT Pub. Date: Apr. 19, 2018

(65) Prior Publication Data
US 2019/0224221 A1     Jul. 25, 2019

Related U.S. Application Data

(60) Provisional application No. 62/406,036, filed on Oct. 10, 2016.

(51) Int. Cl.
| | |
|---|---|
| C07F 5/02 | (2006.01) |
| A61K 31/7135 | (2006.01) |
| A61K 9/107 | (2006.01) |
| A61K 47/54 | (2017.01) |
| A61K 47/69 | (2017.01) |
| A61K 35/00 | (2006.01) |
| A61K 31/69 | (2006.01) |
| A61K 41/00 | (2020.01) |
| A61P 35/00 | (2006.01) |

(52) U.S. Cl.
CPC .............. *C07F 5/022* (2013.01); *A61K 9/107* (2013.01); *A61K 31/69* (2013.01); *A61K 31/7135* (2013.01); *A61K 41/0057* (2013.01); *A61K 47/555* (2017.08); *A61K 47/6929* (2017.08); *A61P 35/00* (2018.01)

(58) Field of Classification Search
None
See application file for complete search history.

(56) References Cited

FOREIGN PATENT DOCUMENTS

| CN | 101565554 B | * 6/2013 | ............. C09B 57/00 |
|---|---|---|---|
| CN | 105732680 A | 4/2016 | |

OTHER PUBLICATIONS

Zhang et al. "Long-Wavelength, Photostable, Two-Photon Excitable Bodipy Fluorophores Readily Modifiable for Molecular Probes" J. Org. Chem. 2013, Vo 78, No. 18, pp. 9153-9160.*
PCT/US17/55243, Int'l Search Report and Written Opinion of the ISA, dated Feb. 5, 2018.
Cheema et al. "Design and synthesis of Bodipy sensitizers with long alkyl chains tethered to N-carbazole and their application for dye sensitized solar cells" Materials Chemistry and Physics, vol. 184, pp. 57-63, Sep. 12, 2016.
Epelde-Elezcano et al. "Modulation of singlet oxygen generation in halogenated BODIPY dyes by substitution at their meso position: towards a solvent-independent standard in the vis region" RSC Advances, vol. 6, pp. 41991-41998, Apr. 21, 2016.
Huang et al. "Ultralow-Power Near Infrared Lamp Lght Operable Targeted Organic Nanoparticle Photodynamic Therapy" J. Am. Chem. Soc., vol. 138, pp. 14586-14591, Oct. 27, 2016.

* cited by examiner

*Primary Examiner* — Joseph R Kosack
(74) *Attorney, Agent, or Firm* — Milstein Zhang & Wu LLC

(57) ABSTRACT

The invention provides a novel class of NIR-absorbing biocompatible organic nanoparticles for effective imaging, targeting and treatment of deep-tissue cancers or tumors. The invention enables a new platform for precise cancer- or tumor-targeting theranostics and clinical cancer treatment.

9 Claims, 29 Drawing Sheets

Scheme 1. a) Schematic illustration of NIR-mediated PDT; b) Car-BDP-TNM construction and molecular structures of Car-BDP, PLA-PEG and PLA-PEG-FA

Scheme 2. Synthesis steps of the photodynamic reagent (Car-BDP) and tumor-targeting polymer.

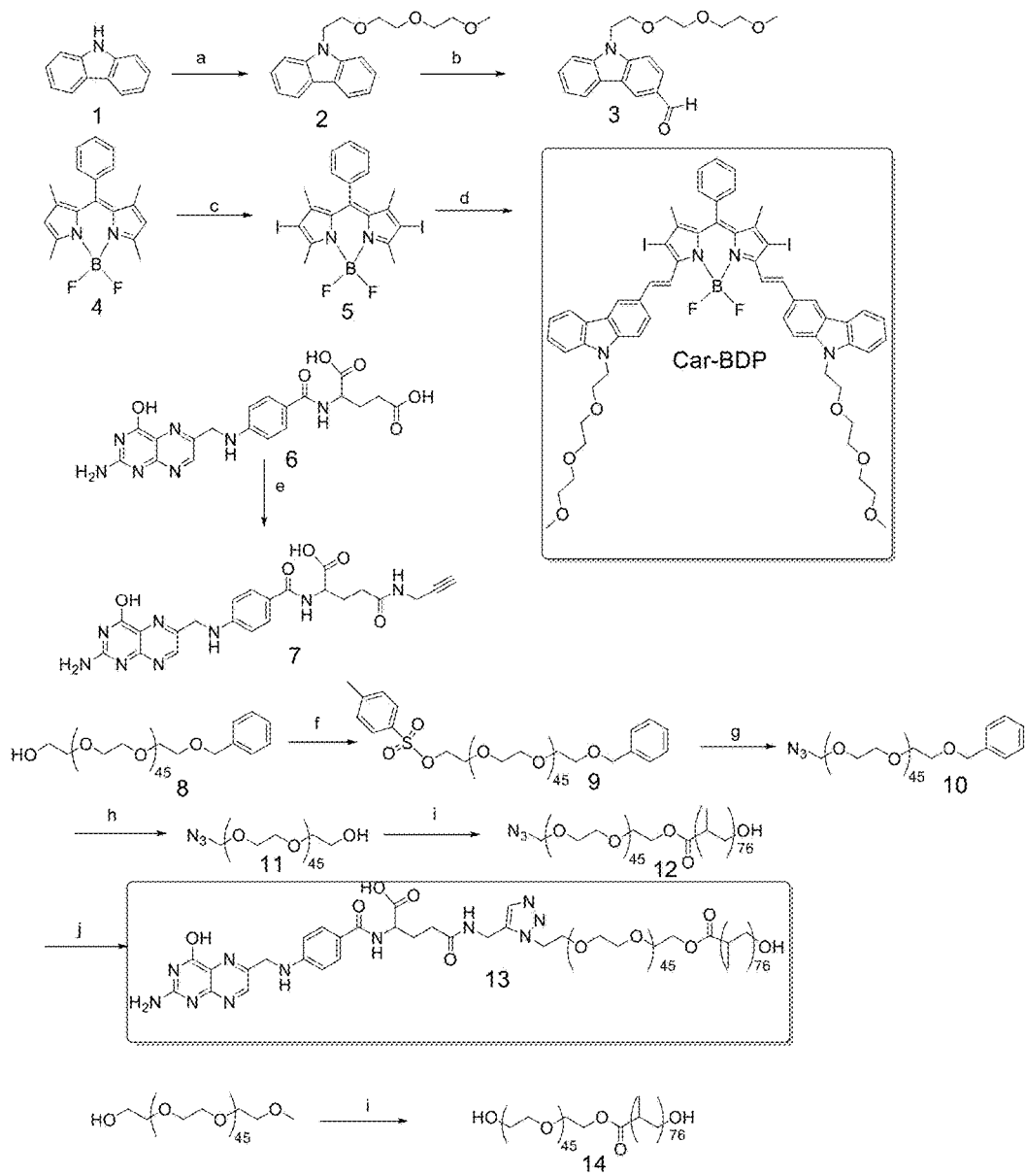

FIG. 2. (a) Tetrabutylammonium iodide, 50% NaOH solution; (b) N,N-dimethylformamide, phosphorus oxychloride; (c) $I_2$, $HIO_3$; (d) acetic acid, piperidine; (e) propargylamine, N,N'-dicyclohexylcarbodiimide (DCC), dimethylformamide (DMSO); (f) triethylamine (TEA), toluenesulfonyl chloride, $CH_2Cl_2$; (g) sodium azide, DMF; (h) 35% HCl solution/tetrahydrofuran (THF) (v/v 1/1); (i) lactide, tin(II) 2-ethylhexanoate; (j) DMSO/$CHCl_3$ (1/1, v/v), $CuSO_4 \cdot 5H_2O$, sodium ascorbate.

*Scheme 3.* Illustration of NIR nanoparticle-mediated PDT procedure.

ULTRALOW-POWER NEAR INFRARED LAMP LIGHT OPERABLE TARGETED ORGANIC NANOPARTICLE PHOTODYNAMIC THERAPY

PRIORITY CLAIMS AND RELATED APPLICATIONS

This application is the U.S. national phase of and claims priority to PCT/US17/55243, filed Oct. 5, 2017, which claims the benefit of priority from U.S. Provisional Application Ser. No. 62/406,036, filed on Oct. 10, 2016, the entire content of each of which is incorporated herein by reference.

TECHNICAL FIELDS OF THE INVENTION

The invention generally relates to materials and methods for photodynamic therapy. More particularly, the invention relates to a novel class of NIR-absorbing biocompatible organic nanoparticles for effective imaging, targeting, delivery of bioactive agent to and treatment of cancers and tumors (e.g., deep-tissue cancers and tumors). The invention provides a new platform for precise cancer or tumor-targeting therapeutic-diagnostic ("theranostics") and clinical treatments.

BACKGROUND OF THE INVENTION

Photodynamic therapy (PDT) is a rapidly developing cancer treatment due to its minimally invasive nature, fewer side effects, and less damage to marginal tissues than that associated with conventional cancer treatments such as chemotherapy and radiotherapy (Photodynamic therapy for cancer. *Nat. Rev. Cancer.* 2003, 3, 380). In the past two decades, PDT has attracted increasing attention, both in fundamental research and clinical practice.

Generally, PDT utilizes a photosensitizer that works as a light-sensitive drug to treat the targeted tissue locally upon irradiation with excitation light at appropriate wavelengths. The mechanism of PDT is based on the interaction between the excited photosensitizer and the surrounding molecules, which generates reactive oxygen species (ROS), such as singlet oxygen ($^1O_2$). ROS in PDT can cause oxidative damage to cancer or tumor cells and, ultimately, be used as a cancer treatment. (Activatable Photosensitizers for Imaging and Therapy *Chem. Rev* 2010, 110, 2839; Imaging and Photodynamic Therapy: Mechanisms, Monitoring, and Optimization *Chem. Rev.* 2010, 110, 2795).

Since near infrared (NIR) light has much deeper tissue penetration than visible light, considerable efforts have been made to develop NIR-light-activated PDT molecules for cancer treatment at the deep-tissue level. (Cancer cell-selective in vivo near infrared photoimmunotherapy targeting specific membrane molecules. *Nat Med.* 2011, 17, 1685; Nanocomposite-Based Photodynamic Therapy Strategies for Deep Tumor Treatment. *Small.* 2015, 11, 5860.)

However, due to their weak absorption and low singlet oxygen quantum yield upon NIR irradiation, the clinical use of PDT for deep-tissue cancer treatment remains challenging. For example, the absorption of the FDA-approved PDT drug PpIX is quite weak in the NIR region. (Cancer cell-selective in vivo near infrared photoimmunotherapy targeting specific membrane molecules. *Nat Med.* 2011, 17, 1685; Nanocomposite-Based Photodynamic Therapy Strategies for Deep Tumor Treatment. *Small.* 2015, 11, 5860.)

To address this issue, lanthanide-doped up-converting nanoparticles (UCNPs) were developed as in vivo photo-transducers that can be excited by NIR light and emit in the visible spectrum, overlapping with the activation wavelengths of PDT drugs. (In vivo photodynamic therapy using upconversion nanoparticles as remote-controlled nanotransducers. *Nat Med.* 2012, 18, 1580; Amplifying the red-emission of upconverting nanoparticles for biocompatible clinically used prodrug-induced photodynamic therapy. *ACS Nano.* 2014, 8, 10621.)

The deep tissue therapeutic outcome, however, remains suboptimal. In addition, the physiological toxicity and systemic clearance of the rare-earth components in inorganic UCNPs remains unclear. (Upconverting nanoparticles: assessing the toxicity. *Chem. Soc. Rev.* 2015, 44, 1561; The biosafety of lanthanide upconversion nanomaterials. *Chem. Soc. Rev.* 2015, 44, 1509.)

Although several photosensitizers such as azo-BODIPY molecules and their loaded nanoparticles were reported, these compounds require a laser beam with relatively high power density (>100 mW cm$^{-2}$) to respond to NIR light activation for PDT. (Vascular-targeted photodynamic therapy with BF$_2$-chelated Tetraaryl-Azadipyrromethene agents: a multi-modality molecular imaging approach to therapeutic assessment. *Br J Cancer.* 2009, 101, 1565). Due to such limitations, these compounds would not be suitable for deep-tissue PDT.

Thus, it is highly desirable to develop organic photosensitizer molecules for deep-tissue tumor PDT, in particular those that are biocompatible, biodegradable and have intensive-absorption and high-singlet-oxygen quantum yield in the NIR region. (Nanoparticles in photodynamic therapy. *Chem Rev.* 2015, 115, 1990; Imaging and photodynamic therapy: mechanisms, monitoring, and optimization. *Chem. Rev.* 2010, 110, 2795.)

SUMMARY OF THE INVENTION

The invention provides a novel class of NIR-absorbing biocompatible organic nanoparticles for effective targeting and treatment of deep-tissue cancers or tumors via precise tumor-targeting theranostics that are suitable clinical cancer treatments.

Deep tissue penetration is a major challenge in practical PDT. Disclosed herein is a novel class of imaging-guidable deep-tissue activatable photosensitizers for PDT, represented by a biocompatible and highly effective NIR-light-absorbing carbazole-substituted BODIPY (Car-BDP) molecule. Car-BDP possesses an intense, broad NIR absorption band (about 600 nm to about 800 nm) with a remarkably high singlet oxygen quantum yield ($\Phi_A$=about 67%). After being encapsulated with biodegradable PLA-PEG-FA polymers, Car-BDP can form uniform, water-soluble and tumor-targeting small organic nanoparticles.

Instead of using laser light, nanoparticles disclosed herein offer an unprecedented deep-tissue, tumor targeting photodynamic therapeutic effect by using an exceptionally low-power-density and cost-effective lamp light (12 mW cm$^{-2}$). In addition, these nanoparticles can be simultaneously traced in vivo due to their excellent NIR fluorescence. The present invention enables a major improvement in PDT added by a new class of NIR-absorbing biocompatible organic nanoparticles for effective targeting and treatment of deep-tissue cancers and tumors. This invention also provides a new platform for precise tumor-targeting theranostics and affordable clinical cancer treatment.

In one aspect, the invention generally relates to a compound having the structural formula:

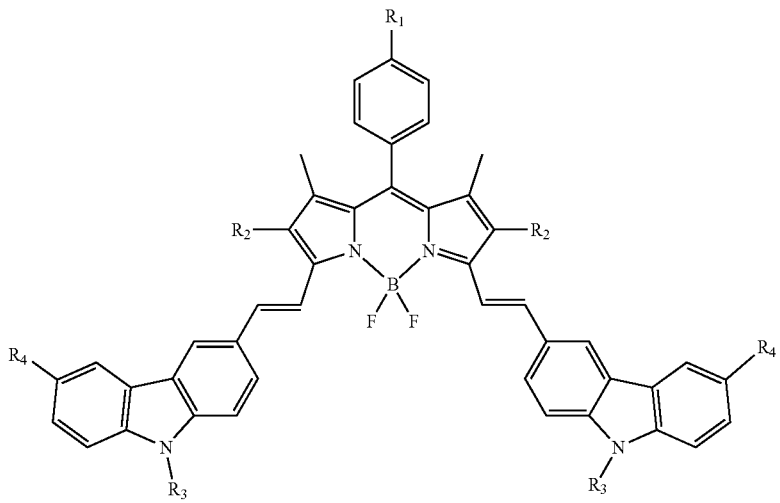

wherein $R_1$ is selected from the group consisting of H, Br, I, alkynyl, alkyl, alkenyl, azide, PEG, amine, carboxyl acid, and hydroxyl groups; each $R_2$ is independently selected from the group consisting of Br and I; each $R_3$ is independently selected from the group consisting of alkynyl, alkyl, alkenyl, azide, PEG, amine, carboxylic acid, and hydroxyl groups; and each $R_4$ is independently selected from the group consisting of H, Br, I, phenyl, and phenylethynyl groups, or a pharmaceutically acceptable form thereof.

In another aspect, the invention generally relates to a nanoparticulate material. The nanoparticulate material includes: a biodegradable amphiphilic polymer nanomicelle; and a compound having the structural formula:

maceutically acceptable form thereof. The compound is encapsulated in the biodegradable polymer nanomicelle.

In yet another aspect, the invention generally relates to a pharmaceutical composition comprising a compound disclosed herein in an amount effective to treat, prevent, or reduce one or more diseases or disorders, in a mammal, including a human, and a pharmaceutically acceptable excipient, carrier, or diluent.

In yet another aspect, the invention generally relates to a nanoparticulate material disclosed herein in an amount effective to treat, prevent, or reduce one or more diseases or disorders, in a mammal, including a human, and a pharmaceutically acceptable excipient, carrier, or diluent.

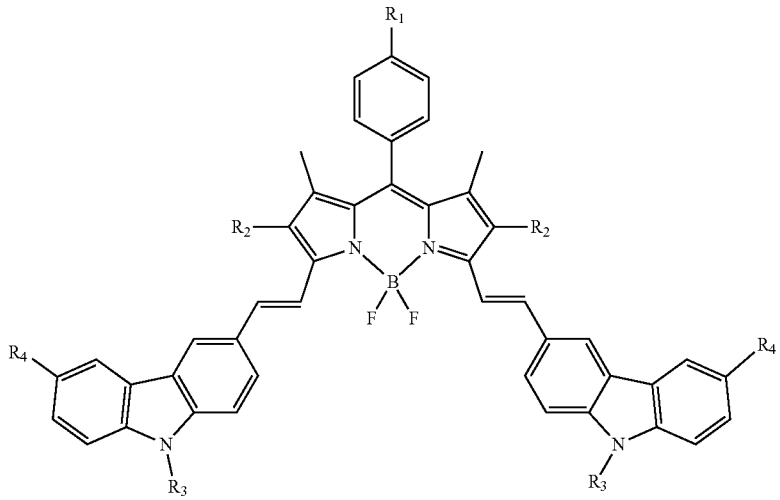

wherein $R_1$ is selected from the group consisting of H, Br, I, alkynyl, alkyl, alkenyl, azide, PEG, amine, carboxyl acid, and hydroxyl groups; each $R_2$ is independently selected from the group consisting of Br and I; each $R_3$ is independently selected from the group consisting of alkynyl, alkyl, alkenyl, azide, PEG, amine, carboxylic acid, and hydroxyl groups; each $R_4$ is independently selected from the group consisting of H, Br, I, phenyl, and phenylethynyl groups, or a phar- In yet another aspect, the invention generally relates to a method for treating a cancer or tumor. The method includes: administering to a subject in need thereof a nanoparticulate material comprising a photosensitizer and a targeting moiety, wherein the photosensitizer is sensitive to excitation in the range from about 600 nm to about 1,000 nm and the targeting moiety has an affinity to a cancer or tumor cell or is preferentially upkate by a cancer or tumor cell; and directing a light beam at a location of the cancer or tumor, wherein the lightbeam comprises a wavelength from about 600 nm to about 1,000 nm.

DEFINITIONS

Figure 1:
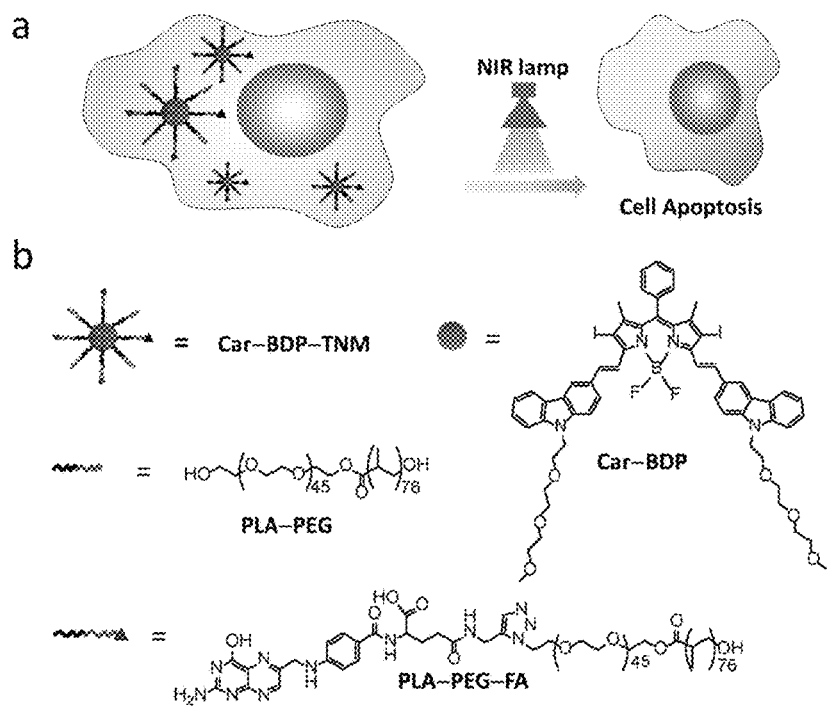
FIG. 1. Scheme 1. *a*) Schematic illustration of NIR-mediated PDT; *b*) Car-BDP-TNM construction and molecular structures of Car-BDP, PLA-PEG and PLA-PEG-FA FIG. 2. Scheme 2. Synthetic steps of the photodynamic reagent (Car-BDP) and tumor-targeting polymer.
Figure 3:
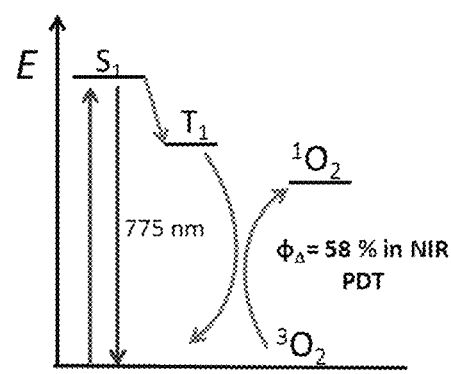
FIG. 3. Scheme 3. Schematic illustration of NIR nanoparticle-mediated PDT procedure.

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

As used herein, "administration" of a disclosed compound encompasses the delivery to a subject of a compound as described herein, or a prodrug or other pharmaceutically acceptable derivative thereof, using any suitable formulation or route of administration, as discussed herein.

As used herein, the terms "cancer" and "tumor" are used interchangeably herein and refer to or describes the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer.

As used herein, the term "therapeutic effect" refers to a therapeutic benefit and/or a prophylactic benefit as described herein. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the terms "effective amount" or "therapeutically effective amount" refer to that amount of a compound or pharmaceutical composition described herein that is sufficient to effect the intended application including, but not limited to, disease treatment, as illustrated below. In some embodiments, the amount is that effective for detectable killing or inhibition of the growth or spread of cancer or tumor cells; the size or number of cancer or tumor; or other measure of the level, stage, progression or severity of the cancer or tumor.

The therapeutically effective amount can vary depending upon the intended application, or the subject and disease condition being treated, e.g., the desired biological endpoint, the pharmacokinetics of the compound, the disease being treated, the mode of administration, and the weight and age of the patient, which can readily be determined by one of ordinary skill in the art. The term also applies to a dose that will induce a particular response in target cells, e.g., reduction of cell migration. The specific dose will vary depending on, for example, the particular compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. Treatment is aimed to obtain beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds. In some embodiments, a "pharmaceutically acceptable form" includes, but is not limited to, pharmaceutically acceptable salts, stereoisomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. *Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchioric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}\ alkyl)^4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a pharmaceutically acceptable ester. As used herein, the term "pharmaceutically acceptable ester" refers to esters that hydrolyze in vivo and include those that break down readily in the human body to leave the parent compound or a salt thereof. Such esters can act as a prodrug as defined herein. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfinic acids, sulfonic acids and boronic acids. Examples of esters include formates, acetates, propionates, butyrates, acrylates and ethylsuccinates. The esters can be formed with a hydroxy or carboxylic acid group of the parent compound.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

Definitions of specific functional groups and chemical terms are described in more detail below. When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, the term "alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents.

DETAILED DESCRIPTION OF THE INVENTION

A biocompatible and highly effective MR-light-absorbing carbazole-substituted BODIPY (Car-BDP) molecule is reported as a class of imaging-guidable deep-tissue activatable photosensitizers for PDT. Car-BDP possesses an intense, broad MR absorption band (600-800 nm) with a remarkably high singlet oxygen quantum yield ($\Phi_\Delta$=67%).

After being encapsulated with biodegradable PLA-PEG-FA polymers, Car-BDP can form uniform and small organic nanoparticles that are water-soluble and tumor targetable. Rather than using laser light, such nanoparticles offer an unprecedented deep-tissue, tumor targeting photodynamic therapeutic effect by using an exceptionally low-power-density and cost-effective lamp light (12 mW cm$^{-2}$). In addition, these nanoparticles can be simultaneously traced in vivo due to their excellent MR fluorescence. This study signals a major step forward in photodynamic therapy by developing a new class of MR-absorbing biocompatible organic nanoparticles for effective targeting and treatment of deep-tissue tumors. This work also provides a potential new platform for precise tumor-targeting theranostics and novel opportunities for future affordable clinical cancer treatments.

Figure 4:
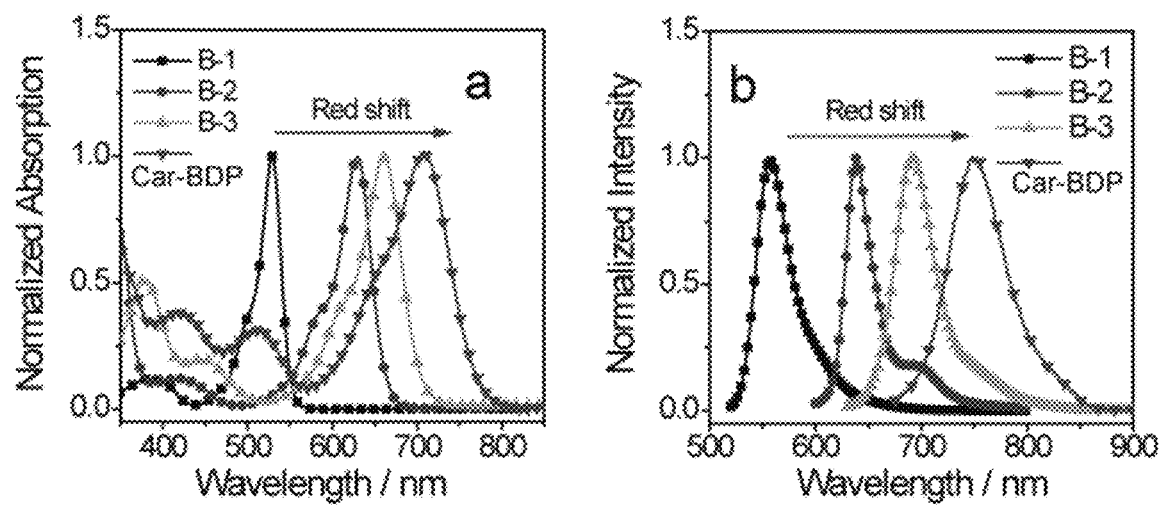
FIG. 4. *a*) Normalized UV-Vis absorption spectra of B-1 to B-3 and Car-BDP; *b*) Normalized fluorescence emission spectra of B-1 to B-3 and Car-BDP.

To achieve PDT in deep-tissue tumors by using only low-power-density cost-effective incoherent lamp-light excitation, a carbazole-substituted BODIPY (Car-BDP) molecule was designed as a new highly MR-sensitive photosensitizer. As shown in Scheme 1 (FIG. 1), compared with currently used BODIPY photosensitizers, such as 2,6-diiodio-BODIPY (B-1, ε=85000 M$^{-1}$ cm$^{-1}$ at 525 nm) and 2,6-diiodiodistyl-BODIPY (B-2, ε=77000 M$^{-1}$ cm$^{-1}$ at 630 nm; B-3, ε=98000 M$^{-1}$ cm$^{-1}$ at 661 nm) (Table 1), BODIPY dimer[28] and BODIPY-modified iridium complexes, Car-BDP presented significantly broader and more intense absorption in the MR region due to the large n-core of the carbazole moiety (FIG. 4a). In addition, the NIR fluorescence of Car-BDP had an emission peak at 755 nm and the fluorescence quantum yield was determined ($\Phi_F$=4%; FIG. 4b). It is worthwhile noting that such high singlet quantum yield alongside strong MR fluorescence is rare due to the fast intersystem-crossing (ISC) rate and the consequent poor fluorescence quantum yield of most conventional used sensitizers. More importantly, it was found that Car-BDP showed a remarkably high singlet-oxygen yield ($\Phi_A$=67%).

Molecular structures of B-1, B-2, B-3, and ZnPc.

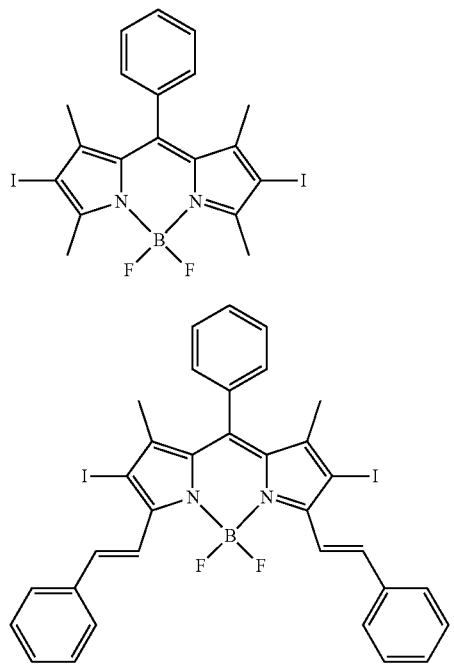

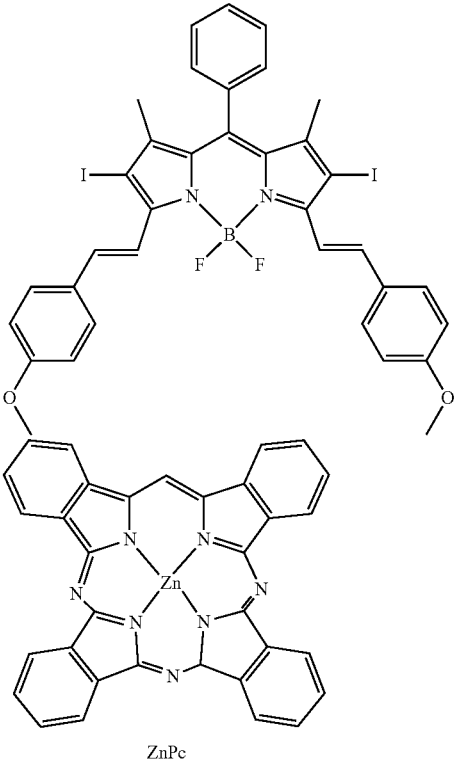

TABLE 1

Photophysical parameters of B-1 to B-3, Car-BDP, and Car-BDP-TNM

| | $\lambda_{abs}$ (max) | ε/10$^5$ M$^{-1}$ cm$^{-1}$ | $\lambda_{em}$ (max) | $\Phi_F$ (%) | $\tau_T$ (s) | $\Phi_A$ (%) |
|---|---|---|---|---|---|---|
| B-1[a] | 529 | 0.85 | 548 | 3 | 84.6 | 79.5 |
| B-2[b] | 630 | 0.77 | 654 | 5 | 1.8 | 69.0 |
| B-3[c] | 661 | 0.98 | 689 | 7 | 1.4 | 61.2 |
| Car-BDP[d] | 709 | 0.99 | 750 | 4[f] | 1.2 ns[g] | 67[h] |
| Car-BDP-TNM[e] | 710 | — | 775 | 1[f] | 0.9 ns[g] | 58[h] |

[a]Reference S2.
[b]Reference S6.
[c]Reference S7.
[d]Recorded in DMSO.
[e]Recorded in PBS.
[f]Fluorescence quantum yield ZnPc (28%) as standard in DMF.
[g]Fluorescence lifetime.
[h]Singlet state oxygen quantum yield with methyl blue ($\Phi_A$ = 52%) as reference.

Figure 5:
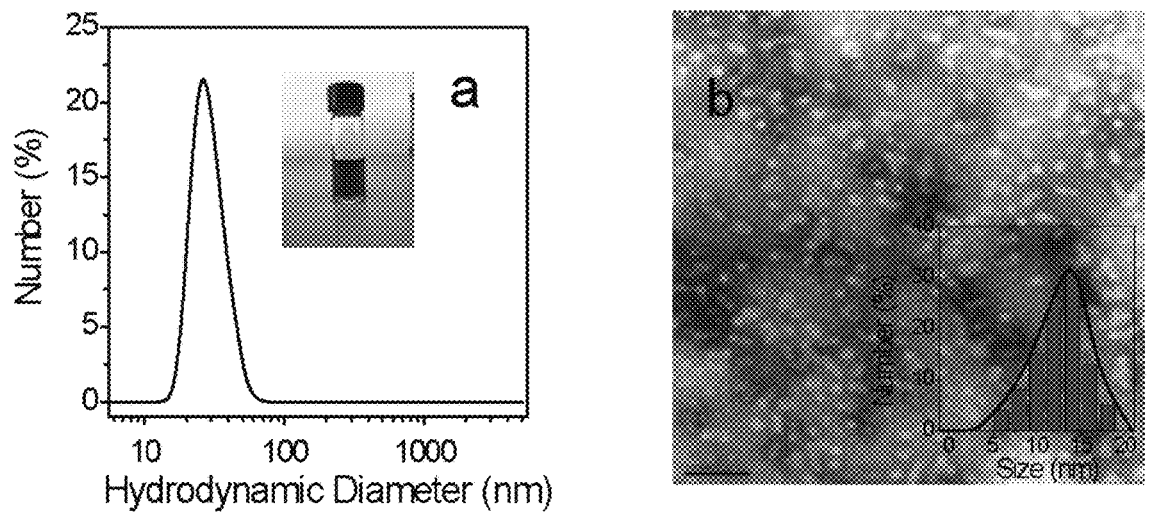
FIG. 5. *a*) Hydrodynamic diameter of Car-BDP-TNM in PBS via dynamic light scattering; inset photograph shows Car-BDP-TNM solution. *b*) TEM image of Car-BDP-TNM stained by phosphotungstic acid, scale bar represents 100 nm.
Figure 13:
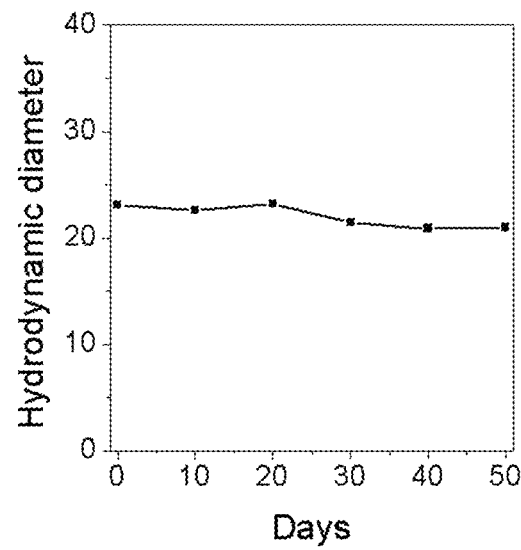
FIG. 13. Colloidal storage stability of Car-BDP-TNM in PBS.

Car-BDP molecule was water solubilized by encapsulating it with tumor targetable amphiphilic polymer PLA-PEG-FA to generate dye-loaded nanomicelles (Car-BDP-TNM); the dye-entrapment efficiency of Car-BDP in the polymer was determined to be high (74%) by the UV-Vis absorption method. Car-BDP-TNM is significantly smaller than previously reported PDT nanoparticles. Firstly, the morphology and size of Car-BDP-TNM were measured by using transmission electron microscopy (TEM). The TEM image in FIG. 5b shows that Car-BDP-TNM consisted of uniform spherical nanoparticles with a diameter of roughly 13.7±3.4 nm. In addition, the hydrodynamic diameter was 23.8±3.2 nm, as measured by dynamic light scattering (DLS) experiments (FIG. 5a). Car-BDP-TNM also showed outstanding colloidal stability in phosphate-buffered saline (PBS); after 50 days, the hydrodynamic diameter remained at 22.2±2.3 nm and no significant aggregation was observed (FIG. 13).

Figure 6:
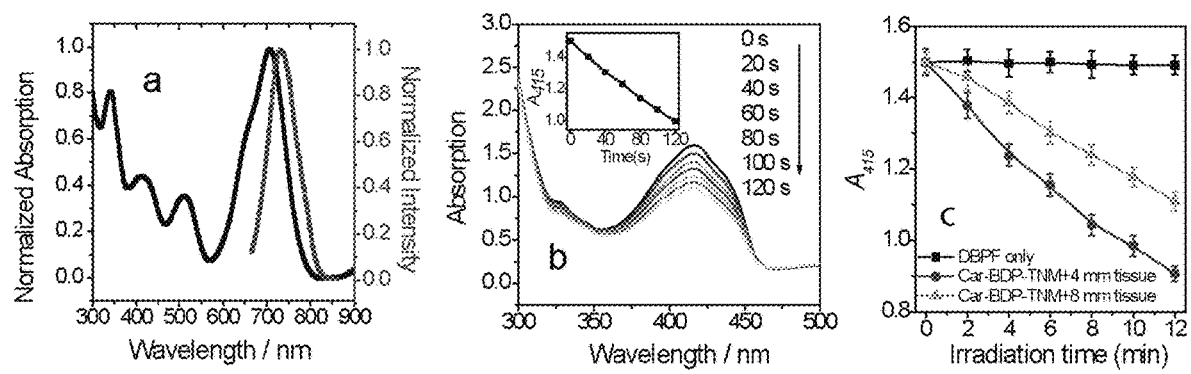
FIG. 6. *a*) Normalized UV-Vis absorption and normalized fluorescence spectra of Car-BDP-TNM in PBS, $\lambda_{ex}$=690 nm. *b*) Changes of DPBF UV-Vis absorption spectra when Car-BDP-TNM was added as photosensitizer. *c*) Plots of change in the optical density of DPBF at 415 nm vs. the irradiation time of pork tissue of different thicknesses, where Car-BDP-TNM was used as the photosensitizer. In PBS having 10% THF, the excitation ranged from 670 nm-800 nm, with a power intensity of 12 mW cm$^{-2}$ of halogen lamp light.
Figure 14:
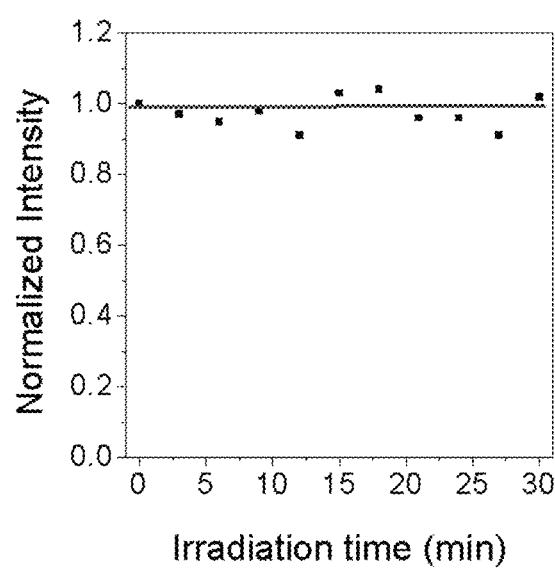
FIG. 14. Photostability of Car-BDP-TNM under 670-800 nm MR light (12 mW cm$^{-2}$) irradiation within 30 min by fluorescence spectra method.
Figure 15:
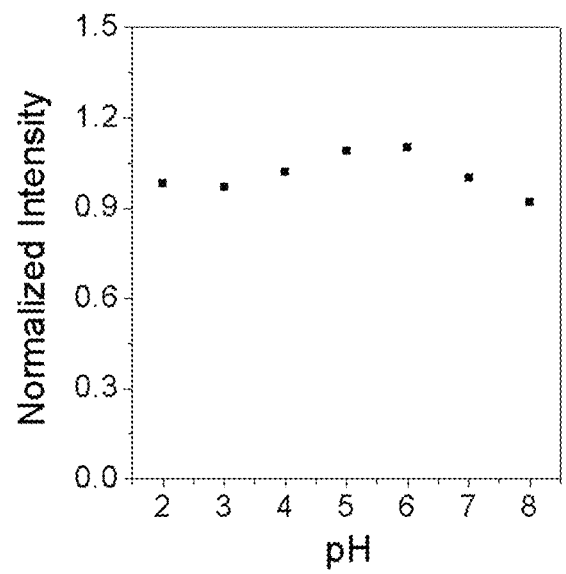
FIG. 15. Influence of pH on the fluorescence intensity of Car-BDP-TNM ($\lambda_{ex}$=690 nm, $\lambda_{em}$=775 nm) in a citric acid-Na$_2$HPO$_4$ buffer.

Next, the photophysical properties of Car-BDP-TNM were measured in PBS; the nanoparticles exhibited intense and broad absorption in the MR from 650-800 nm (FIG. 6a). Car-BDP-TNM displayed near infrared emission in PBS ($\Phi_F$=1%). This excellent MR florescence property enables these organic nanoparticles to be simultaneously traced in vivo during the PDT. The singlet oxygen ($^1O_2$) quantum yield ($\Phi_A$) induced by Car-BDP-TNM ($\Phi_A$=58%) under 710-nm light irradiation from an Horiba spectrometer was evaluated with 1,3-diphenylbenzofuran (DPBF) as an $^1O_2$ indicator.[31] As illustrated in FIG. 6b, upon adding Car-BDP-TNM to the solution, the absorption of the DBPF solution decreased significantly at a wavelength of 415 nm over 120 s of MR irradiation under a ultralow-power-intensity (12 mW cm$^{-2}$) incoherent halogen lamp light irradiation (band pass filter 670-800 nm), which indicates efficient generation of singlet oxygen species. Singlet oxygen generation at the deep-tissue level was also measured (FIG. 6c) using varied thicknesses of pork tissue under a lamp light source. Even when the tissue was as thick as 8 mm, it was still observed a significant decline in DPBF absorption. Such efficient singlet oxygen production in an aqueous solution is indeed essential for deep-tissue PDT. Moreover, Car-BDP-TNM exhibited superior photostability (FIG. 14) and excellent pH stability (FIG. 15), both of which are critical for biomedical applications.

Figure 7:
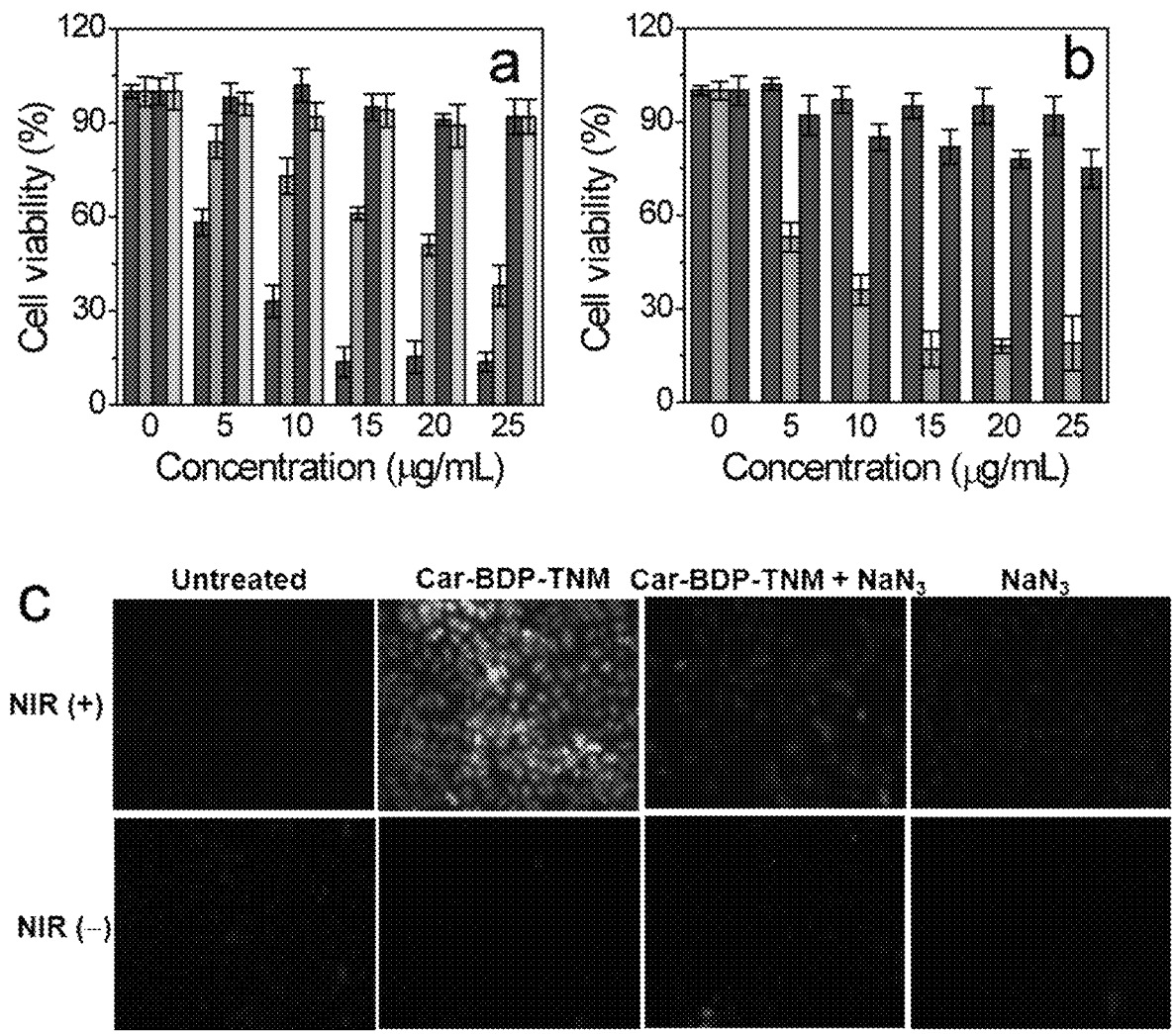
FIG. 7. *a*) MTT assay of HeLa cells viability of different concentrations of Car-BDP-TNM and Car-BDP-NNM: Car-BDP-TNM+NIR (red), Car-BDP-NNM+NIR (green), Car-BDP-TNM+dark (blue), and Car-BDP-NNM+dark (cyan) after treatment. *b*) Sodium azide inhibition as measured by MTT assay for different concentrations of Car-BDP-TNM+dark (red), Car-BDP-TNM+NIR (green), and Car-BDP-TNM+NIR+NaN$_3$ (50 µM) (blue). *c*) Fluorescence microscopy of DCFDA verified singlet-oxygen generation in Car-BDP-TNM (10 µg mL$^{-1}$); mediated intracellular $\lambda_{ex}$=476 nm, emission detection wavelength 485-520 nm.
Figure 18:
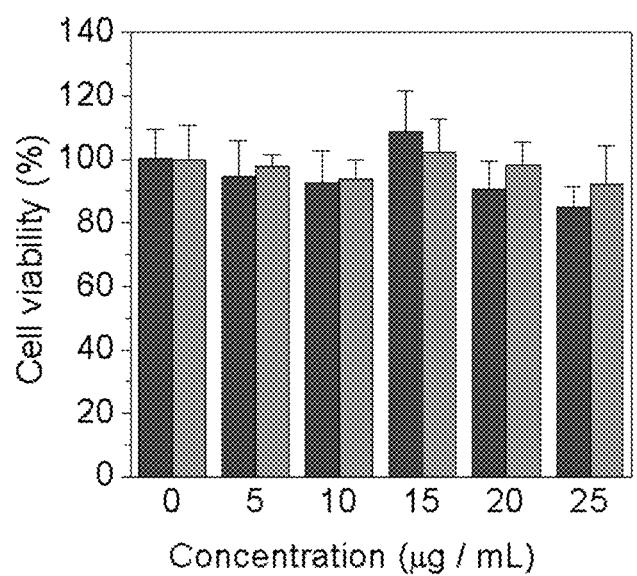
FIG. 18. MTT assay of HeLa cells in different concentration of ZnPc-NM, red column is in dark conditions, green column is under irradiation of 670-800 nm light, 12 mW cm$^{-2}$.
Figure 19:
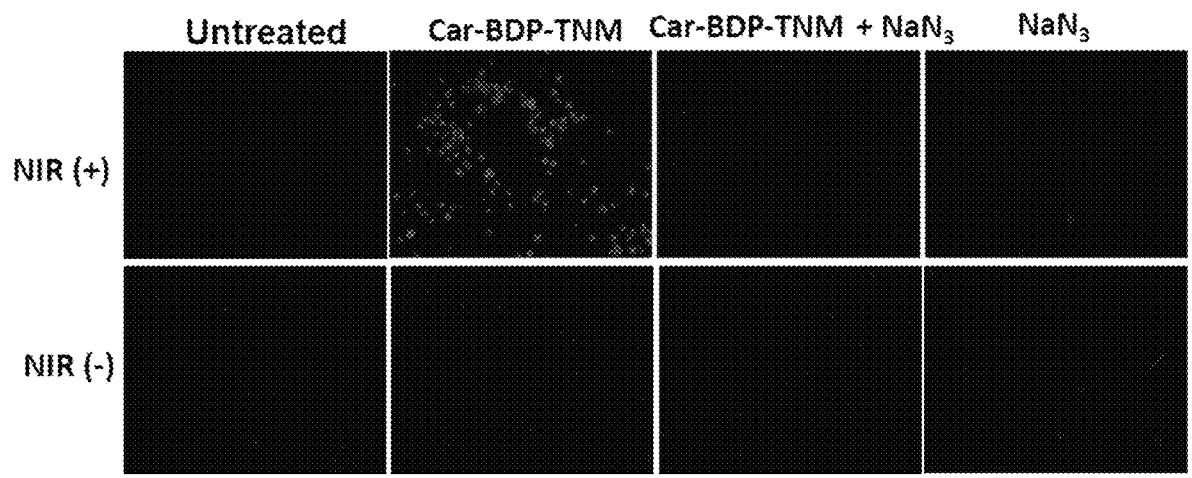
FIG. 19. Fluorescence microscopy observed Car-BDP-TNM (10 µg mL$^{-1}$) mediated MR PDT HeLa cells with PI staining dead cells, $\lambda_{ex}$=530 nm, absorption wavelength 580-650 nm FIG. 20. In vitro PDT assay of 4T1 cells using Car-BDP-TNM and PI as dead cells staining (10 µg mL$^{-1}$, 670-800 nm lamp light irradiation 10 min, 12 mW cm$^{-2}$) observed by fluorescence microscopy. $\lambda_{ex}$=530 nm, emission detection wavelength 580-650 nm.
Figure 20:
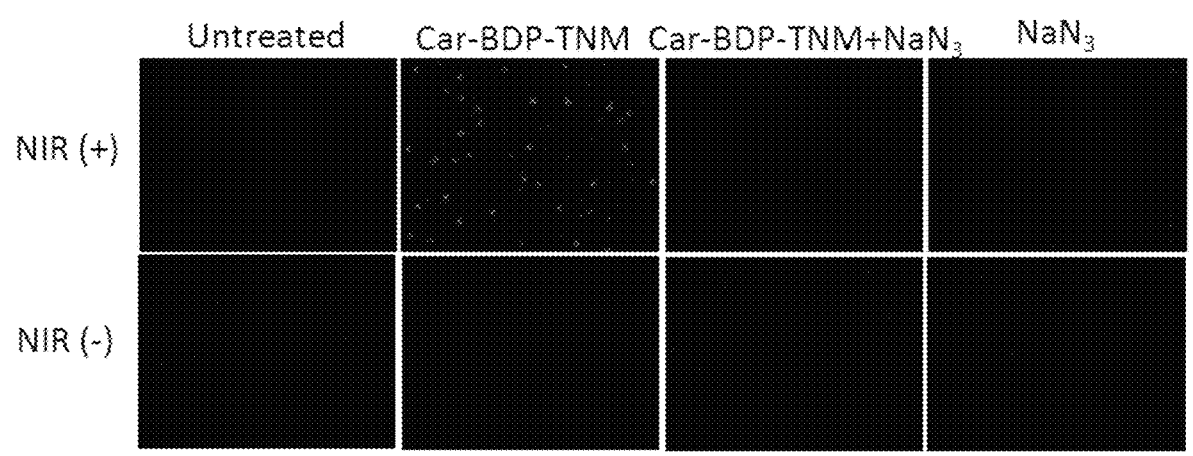
Figure 21:
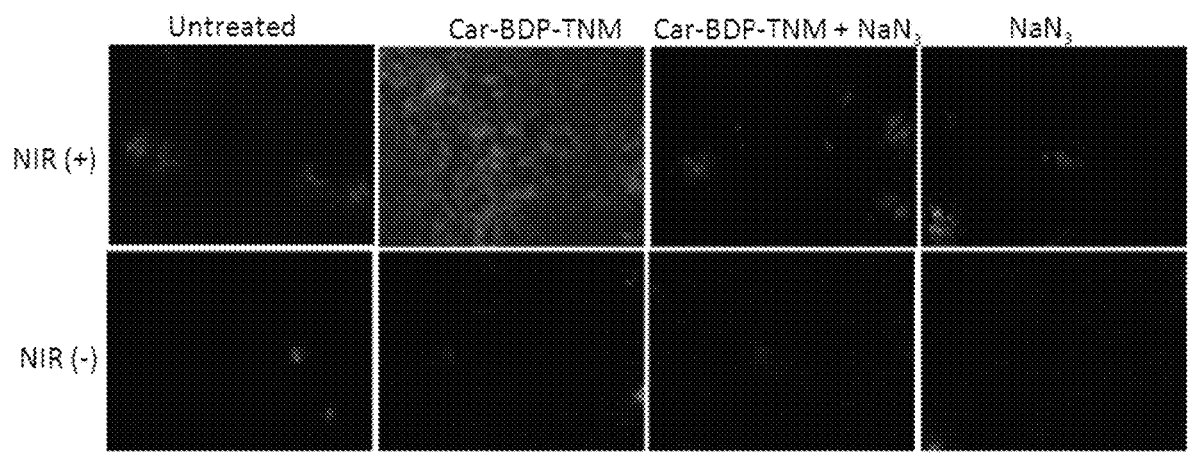
FIG. 21. Intracellular generation of singlet oxygen in Car-BDP-TNM treated 4T1 cell line verified by DCFDA. Car-BDP-TNM concentration, 10 µg mL$^{-1}$, irradiated at 670-800 nm, 12 mW cm$^{-2}$, for 10 min. NaN$_3$ concentration, 50 µM. Imaging setting, $\lambda_{ex}$=476 nm, emission detection wavelength 485-520 nm.

A successful PDT photosensitizer needs to exhibit low cytotoxicity in the dark but significant cancer cell death when exposed to light. In in vitro study, the cytotoxicity of the Car-BDP-TNM to HeLa cells was examined by using the MTT assay, both in the presence and the absence of irradiation with 670-800 nm light (FIG. 7a). In the absence of light, the Car-BDP-TNM was negligibly cytotoxic. In contrast, it exhibited high cytotoxicity under irradiation with the aforementioned 670-800 nm light (power intensity of 12 mW cm$^{-2}$). In addition, Car-BDP-TNM showed excellent inhibition of growth of 4T1 cells (breast cancer cells; FIG. 8c and S10). Car-BDP-TNM-mediated PDT nanoparticles are superior to the widely used ZnPc counterpart nanoparticles (ZnPC-NM) with the same excitation source and power intensity (FIG. 18).

Figure 16:
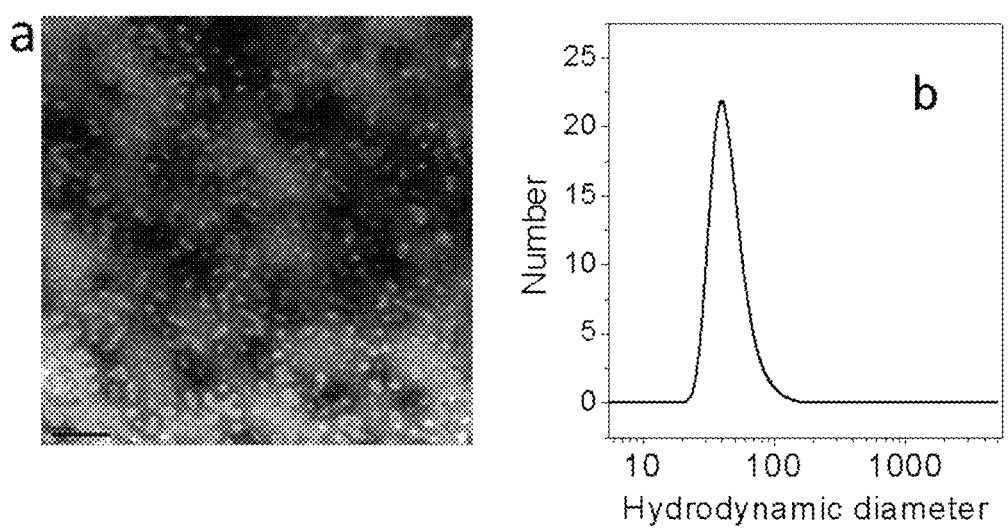
FIG. 16. *a*) TEM image of Car-BDP-NNM stained by phosphotungstic acid, scale bar represents 100 nm, *b*) hydrodynamic diameter of Car-BDP-NNM in PBS, units (nm).
Figure 17:
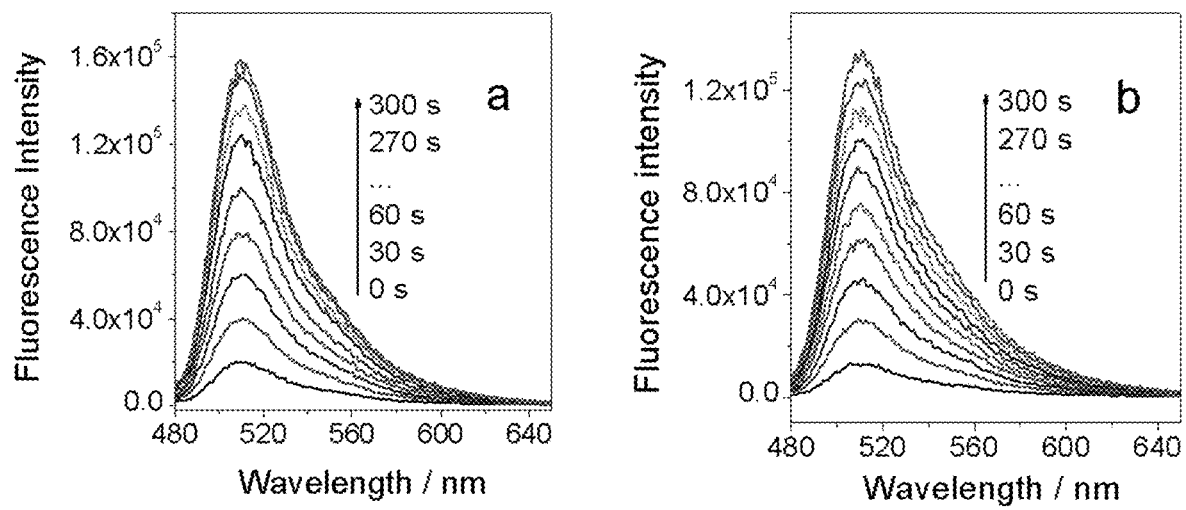
FIG. 17. Changes of fluorescence spectra of SOSG in the appearance of *a*) Car-BDP-TNM and *b*) Car-BDP-NNM as photosensitizers (10 µg mL$^{-1}$) in PBS under irradiation of lamp light (670-800 nm, 12 mW cm$^{-2}$) for 300 s.
Figure 22:
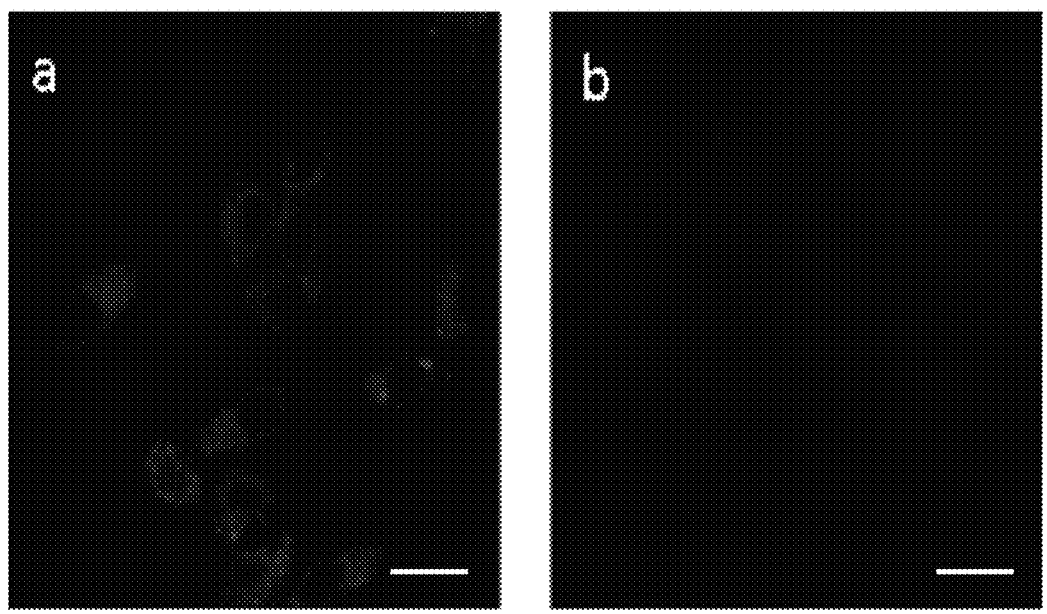
FIG. 22. *a*) Car-BDP-TNM and *b*) Car-BDP-NNM taken up by HeLa cells (cervical cancer cells) verified by confocal fluorescence imaging. Incubated time 12 h, $\lambda_{ex}$=633 nm, emission detection wavelength 680-850 nm, scale bar represents 30 µm.
Figure 23:
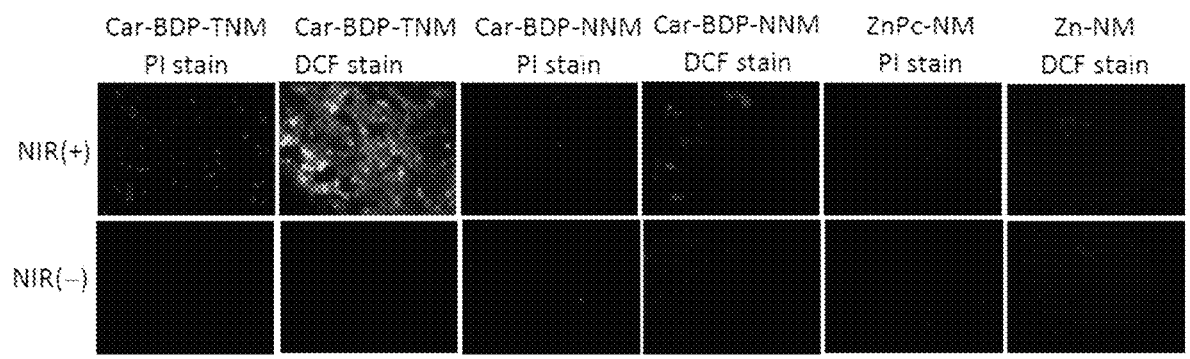
FIG. 23. DCF staining and PI staining HeLa cells in different conditions. Car-BDP-TNM, Car-BDP-NNM, and ZnPc-NM as photosensitizers (10 µg mL$^{-1}$, 670-800 nm irradiation 10 min, 12 mW cm$^{-2}$), MR (+) means irradiation, MR (−) means dark conditions. For the DCF staining, $\lambda_{ex}$=476 nm, capture wavelength 485-520 nm; For the PI staining, $\lambda_{ex}$=530 nm, emission detection wavelength 580-650 nm.

Then studied was the tumor-cell-targeting ability of these nanoparticles with and without the inclusion of folate ligands. As a control, a PLA-PEG polymer was adopted to encapsulate the Car-BDP to generate folate-free nanomicelles (Car-BDP-NNM) (FIG. 16). HeLa cells with Car-BDP-TNM fluoresced more brightly than those with Car-BDP-NNM (FIG. 22). This result shows that folate ligands indeed improve the uptake of nanoparticles. Also conducted was MTT assays to evaluate Car-BDP-TNM and Car-BDP-NNM-induced PDT effects. FIG. 7a showed that Car-BDP-TNM leads to significantly more death in cancer cells than Car-BDP-NNM. Also compared was the phototoxicity of the system to cancer cells (i.e., HeLa) and normal cells (i.e., human skin epidermal Greengo cells). Clearly, Car-BDP-TNM had a higher cell-killing effect in cancers than in normal healthy tissue Cell. (FIG. 8b).

Further, the mechanism of Car-BDP-TNM-mediated PDT was validated by using fluorescence microscopy imaging with 2,7-dichlorofluorescein diacetate (DCFDA), a standard fluorescent indicator for singlet-oxygen generation in living cells. (Idris, N. M.; Gnanasammandhan, M. K.; Zhang, J.; Ho, P. C.; Mahendran, R.; Zhang, Y Nat. Med. 2012, 18, 1580.) Here, bright green fluorescence in HeLa cells was observed in the presence of Car-BDP-TNM. However, in the absence of light and sensitizer, no green fluorescence was observed. Sodium azide, a widely accepted singlet-oxygen scavenger was also used in the control experiments. (Hu, J.; Tang, Y. A.; Elmenoufy, A. H.; Xu, H. B.; Cheng, Z.; Yang, X. L. Small. 2015, 11, 5860.) In the presence of sodium azide (FIG. 7c), green fluorescence was not observed, indicating that sodium azide efficiently inhibited singlet-oxygen production and prevented cancer-cell death. These results clearly reveal that the generation of $^1O_2$ in Car-BDP-TNM-mediated PDT is in fact responsible for the death of cancer cells.

Figure 8:
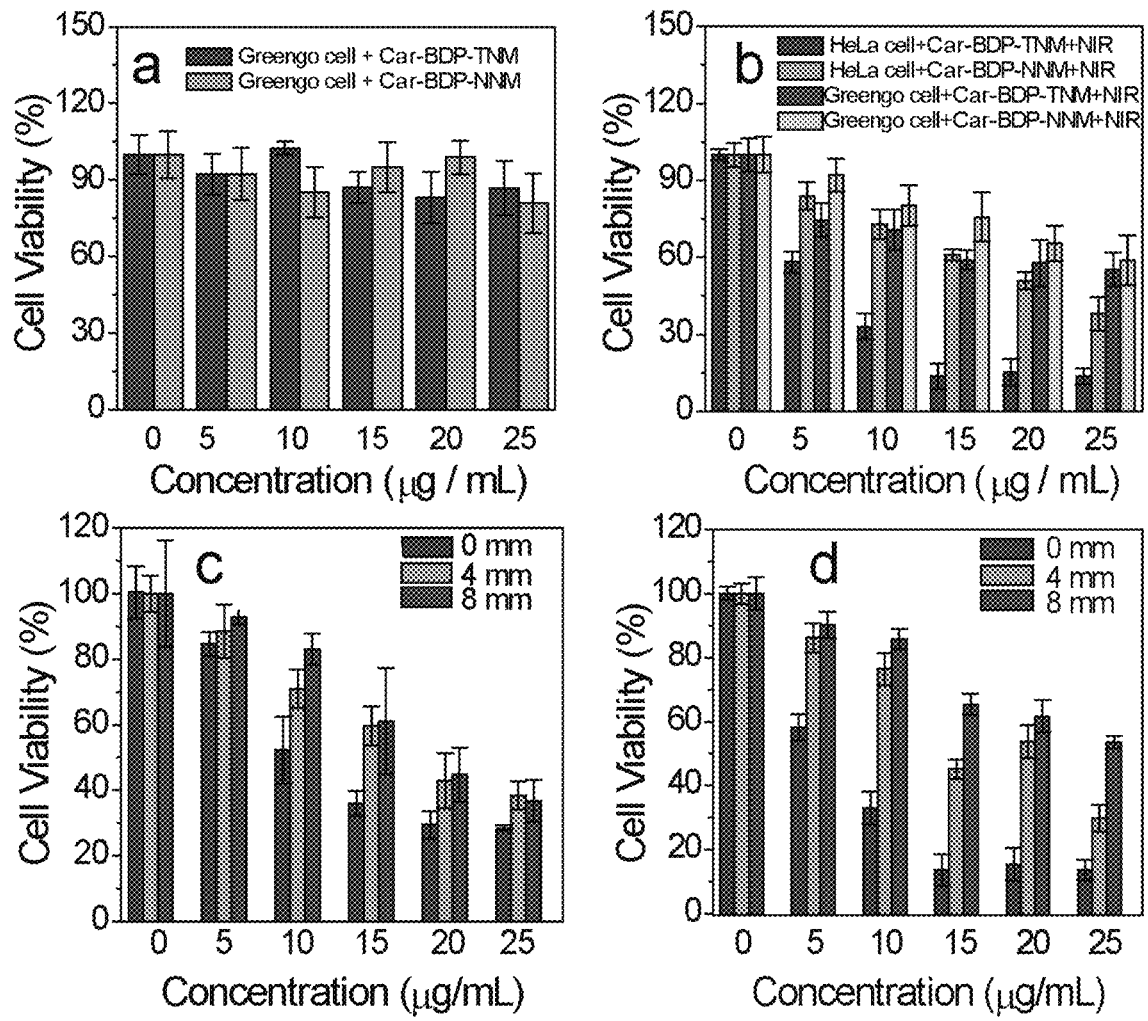
FIG. 8. *a*) Greengo cell viability by MTT assay in different concentration of Car-BDP-TNM and Car-BDP-NNM in the dark; *b*) Compared with Greengo cells and HeLa cells viability in different concentration of Car-BDP-TNM and Car-BDP-TNM under NIR irradiation; Car-BDP-TNM mediated NIR deep tumor conditions in an in vitro MTT assay under different thickness tissue; *c*) 4T1 cell viability. *d*) HeLa cell viability. Tissue thickness was 0, 4, and 8 mm; the excitation ranged from 670 nm-800 nm, with a power intensity of 12 mW cm$^{-2}$ halogen lamp light.
Figure 24:
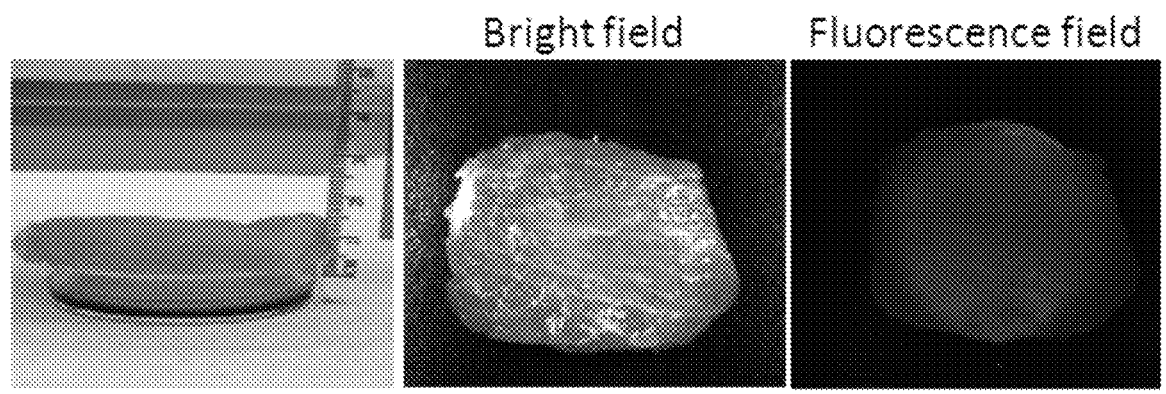
FIG. 24. Deep tissue photographs of fluorescence image of Car-BDP-TNM (25 µg mL$^{-1}$) with caliper animal image instrument couple with a CCD camera. $\lambda_{ex}$=720 nm (3 mW cm$^{-2}$), capture wavelength 730-850 nm, the red color is a pseudo color, the tissue thickness up to 8 mm, exposure time is 250 ms.
Figure 25:
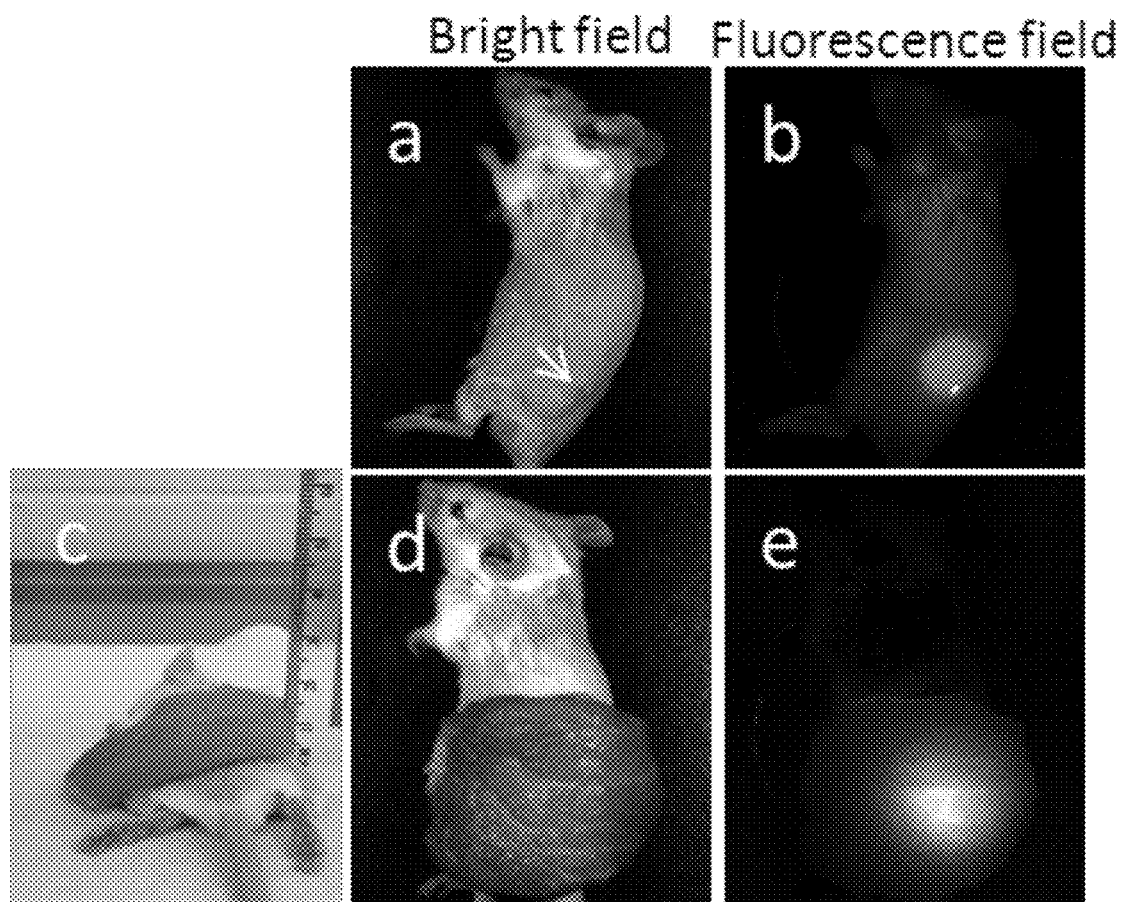
FIG. 25. Fluorescence imaging and simulated deep tissue imaging of a Balb/c mice subcutaneously injected with Car-BDP-TNM (25 µg mL$^{-1}$, 15=720 nm (3 mW cm$^{-2}$), capture wavelength 730-850 nm. white color is pseudo color. The exposure time for (*b*) and (*c*) was 50 and 250 ms, respectively.

To explore whether Car-BDP-TNM can induce tumor cell death in a simulated deep-tissue setting, Car-BDP-TNM-mediated PDT in different tissue thicknesses was measured by using MTT assay. Car-BDP-TNM exhibited significant cell cytotoxicity at 0-, 4-, 8-, mm tissue thickness after 30 min of irradiation at 670-800 nm lamp light (power intensity of 12 mW cm$^{-2}$; FIG. 8). Moreover, the fluorescence of Car-BDP-TNM was detectable even through an 8-mm pork tissue by using an animal imaging instrument (FIGS. 24 and 25). This result indicates simultaneously imaging of the nanoparticles in vivo while using them for therapy.

Figure 9:
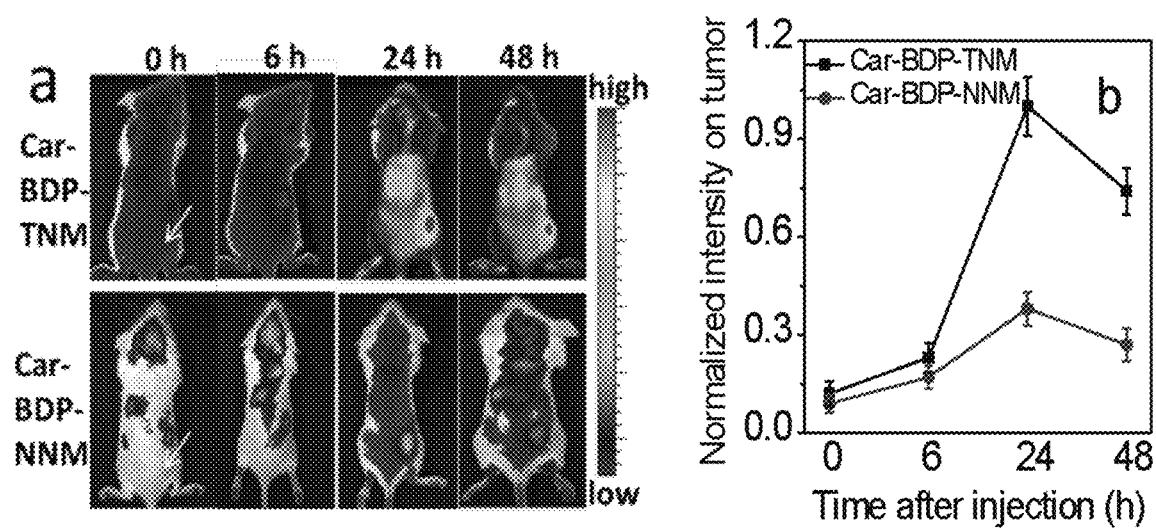
FIG. 9. Specific-targeted NIR fluorescence tumor imaging in vivo. The arrows show the tumor sites. *a*) Time-dependent in vivo NIR fluorescence images of 4T1 tumor-bearing mice after intravenous injection of 50 µg mL$^{-1}$, 150 µL, Car-BDP-TNM as positive group, and Car-BDP-NNM as negative group. *b*) The normalized fluorescence intensity of Car-BDP-TNM and Car-BDP-NNM in 4T1 tumors at 6, 24, and 48 h. Data are means±s.e.m (n=3 mice).

To verify the targeted tumor-killing effect of Car-BDP-TNM in vivo, mice bearing a subcutaneous 4T1 tumor xenograft was chosen as model. To explore the best accumulation time point of photosensitizer for PDT in the tumor tissue, the 4T1 tumor-bearing mice were intravenously injected with Car-BDP-TNM (50 μg mL$^{-1}$, 150 μL), and subjected to in vivo imaging at different time points (FIG. 9a). As an additional control, Car-BDP-NNM (50 μg mL$^{-1}$, 150 μL) was also intravenously injected. The fluorescence at the tumor site increased gradually and reached a maximum level 24 h postinjection (FIG. 9a). After 48 h, the fluorescence intensity of Car-BDP-TNM in the 4T1 tumor gradually decreased. However, the Car-BDP-NNM-treated mice display a much weaker contrast between normal and tumor tissues. This result demonstrates that folate actually improved the nanoparticle targeting to the tumor.

Also observed was the clearance in the liver of Car-BDP-TNM in the same group of living tumor-bearing mice (FIG. 26). 6 h after injection, a fluorescence signal started to appear in the liver. In the 6- to 24-h period, the fluorescence signal in the liver constantly increased. After 48 h, the fluorescence signal from the liver decreased, and after 96 h it had almost completely disappeared. This result indicates that the small size of the nanoparticles may be beneficial to the exclusion of Car-BDP-TNM by the liver.

Figure 10:
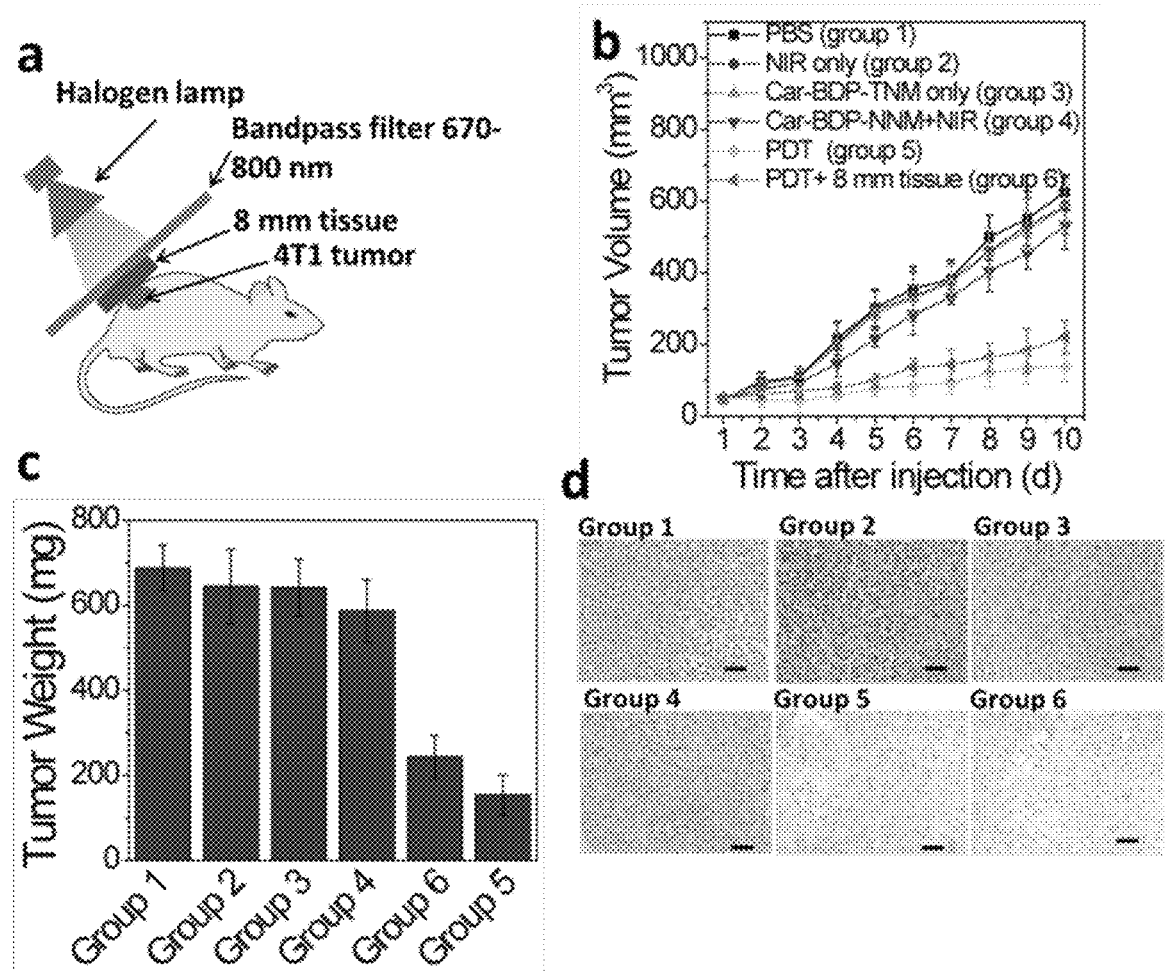
FIG. 10. *a*) Schematic illustration of Car-BDP-TNM-mediated PDT in deep tumor. *b*) Tumor growth inhibition by Car-BDP-TNM-mediated PDT in 4T1 tumors; PDT was performed 24 h after injection of Car-BDP-TNM (50 µg mL$^{-1}$, 150 µL). Values are means±s.e.m. (n=5 mice per group). *c*) Average weights of tumors at day 10. Mice were killed, and tumors isolated for weighing. Values are means±s.e.m. (n=5 mice per group). *d*) H&E staining of tumor-tissue sections from different treatment groups 10 days after treatment; scale bar represents 50 µm.
Figure 11:
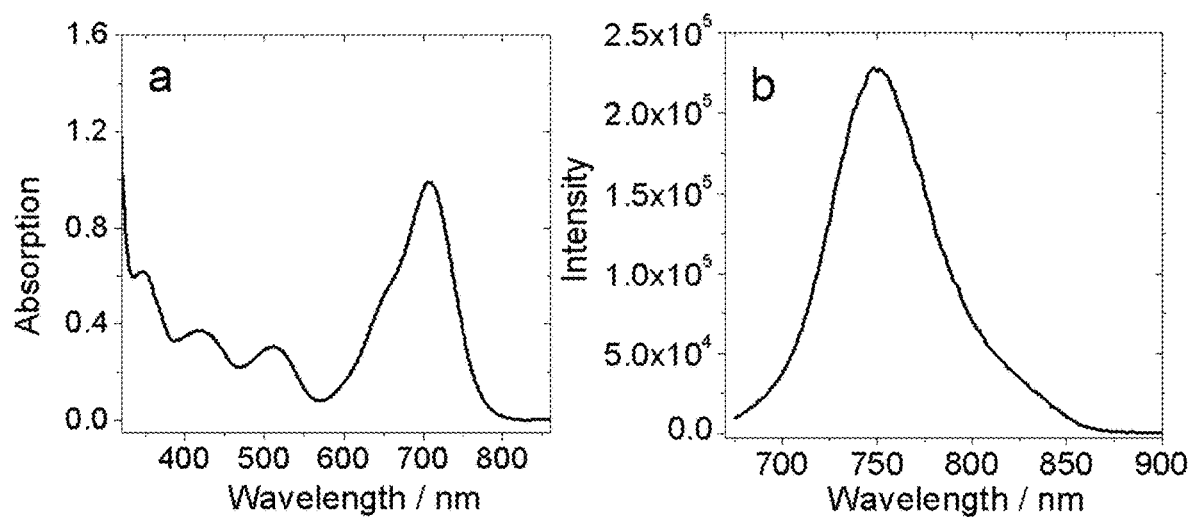
FIG. 11. *a*) UV-Vis absorption spectrum of Car-BDP; *b*) Fluorescence spectrum of Car-BDP, excited at 670 nm, in DMSO. (c=1.0×10$^{-5}$M, 22° C.).
Figure 12:
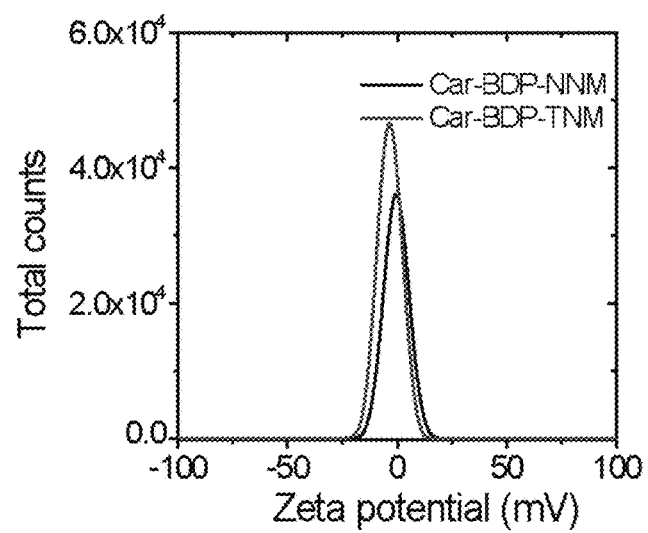
FIG. 12. Zeta potential of Car-BDP-TNM and Car-BDP-NNM in PBS.
Figure 27:
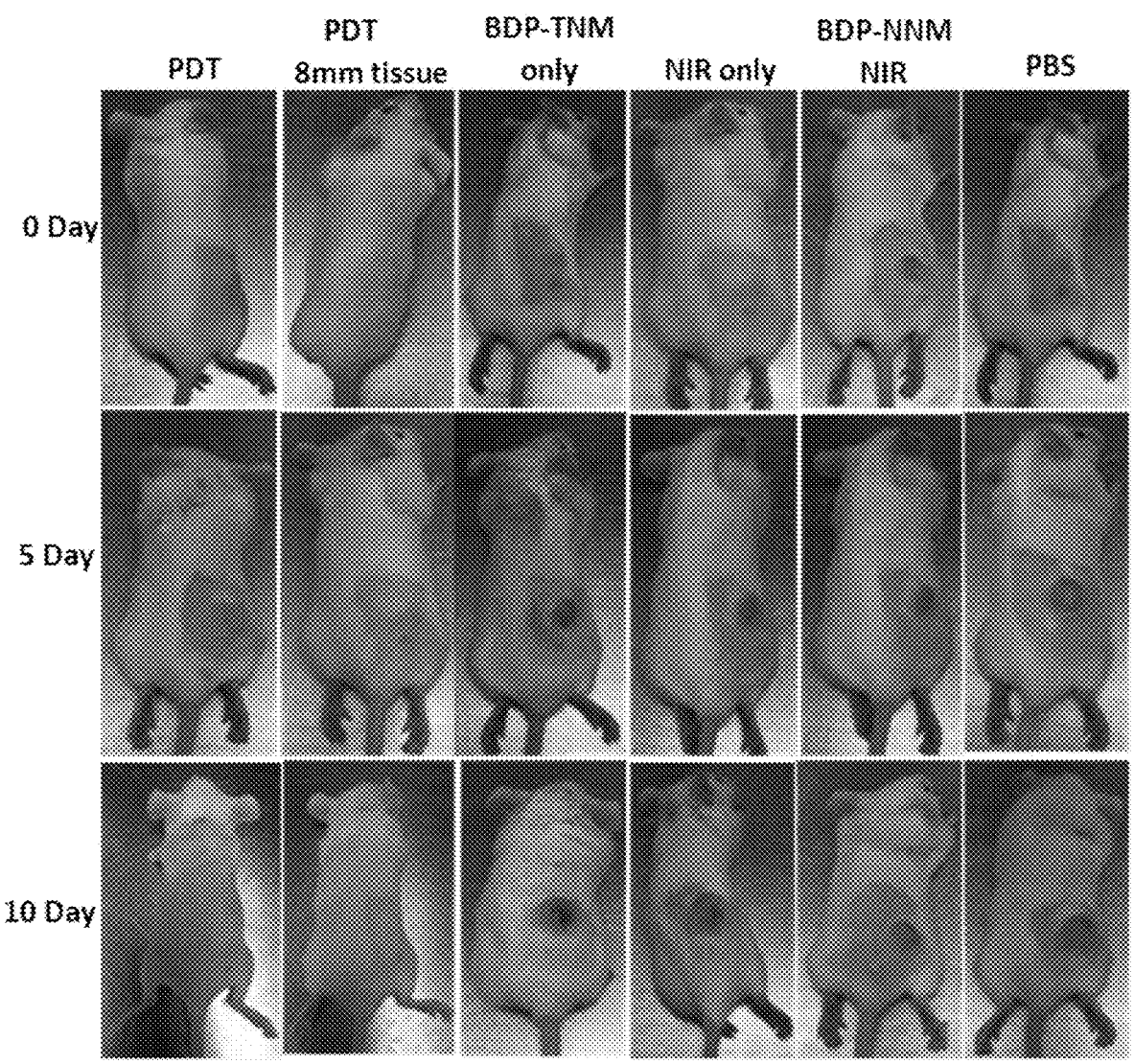
FIG. 27. Photos of representative mice at 0, 5, and 10 day post-treatment after various treatments.

As the accumulation of Car-BDP-TNM in the tumor reached its maximum at 24 h (FIG. 9a), next examined was the effect of treatment with Car-BDP-TNM by irradiating with lamp light (670-800 nm, 12 mW cm$^{-2}$) 24 h post-intravenous injection. For in vivo PDT treatment, the 4T1 tumor-bearing mice were randomly divided into six groups, each group containing five mice: PBS control group (group 1), treated with light irradiation only (group 2), Car-BDP-TNM-intravenous-injected only (group 3), folate-free Car-BDP-NNM-intravenous-injected and then irradiated (group 4), Car-BDP-TNM-intravenous-injected and then treated with irradiation (group 5), and Car-BDP-TNM-intravenous-injected and then irradiated to a penetration depth of 8 mm into tissue (group 6). The PDT treatment was conducted 24 h after intravenous injection. The irradiation was performed with a 670-800 nm at 12 mW cm$^{-2}$ for 30 min (FIG. 10a). After treatment, the therapeutic effects were assessed by monitoring the change in tumor volume (FIG. 10b) and tumor weight (FIG. 10c) as well as by hematoxylin and eosin (H&E) staining of the tumor tissues (FIG. 10d). No tumor growth inhibition or tumor-tissue necrosis was observed in the group of mice with MR only (groups 2), which indicated that irradiation with such a low power intensity MR had little photothermal effect. In group 3, no tumor inhibition was observed, which showed that Car-BDP-TNM has negligible dark toxicity. Group 4 (Car-BDP-NNM) also did not display an obvious therapeutic effect, which indicates that folate was important for targeting tumor tissue. In contrast, the tumor growths of treatment group 5 and 6 (0 and 8 mm screening by external tissue, respectively) were remarkably suppressed. For group 5, tumor volume inhibition efficiency was found to be around 90% and tumor-tissue weight was also significantly less (ca. 150 mg) in comparison to around 700 mg in the PBS control group (FIG. 10c). From the H&E staining analysis, the tumor tissue also showed clear necrosis, which indicates that Car-BDP-TNM can be effectively activated by MR lamp irradiation to be intensely phototoxic to the tumor. More importantly, in group 6, tumor volume inhibition efficiency was observed to be well preserved (ca. 80%) and tumor-tissue weight was about 210 mg, which clearly indicates that Car-BDP-TNM is activated in deep tissue (8 mm) and generates an effective PDT process (FIG. 27). To our knowledge, this is the first time that deep-tissue setting tumor treatment was realized with such a low-power, incoherent MR lamp irradiation.

Figure 26:
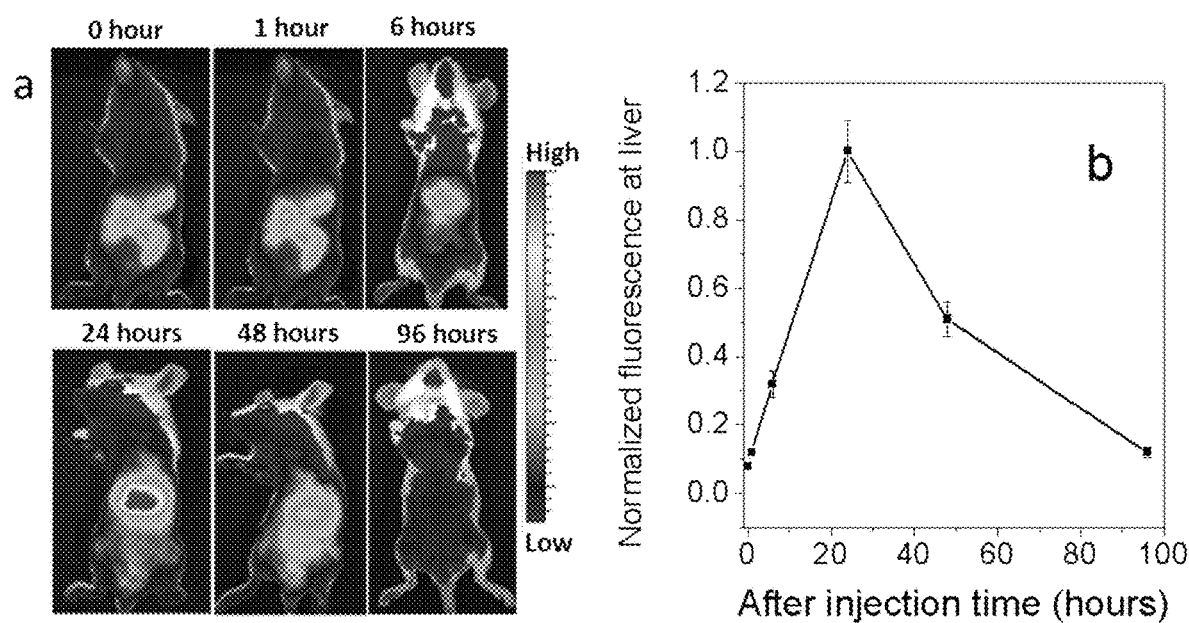
FIG. 26. Car-BDP-TNM accumulation in liver in different time (0 to 96 h), Car-BDP-TNM was injection intravenously (150 μL, 25 μg L$^{-1}$). (a) Fluorescence imaging of mice, excitation filter was Cy5.5, emission filter ICG. (b) Normalized fluorescence intensity at liver at different time-points; error bars indicate standard deviations; N=3.
Figure 28:
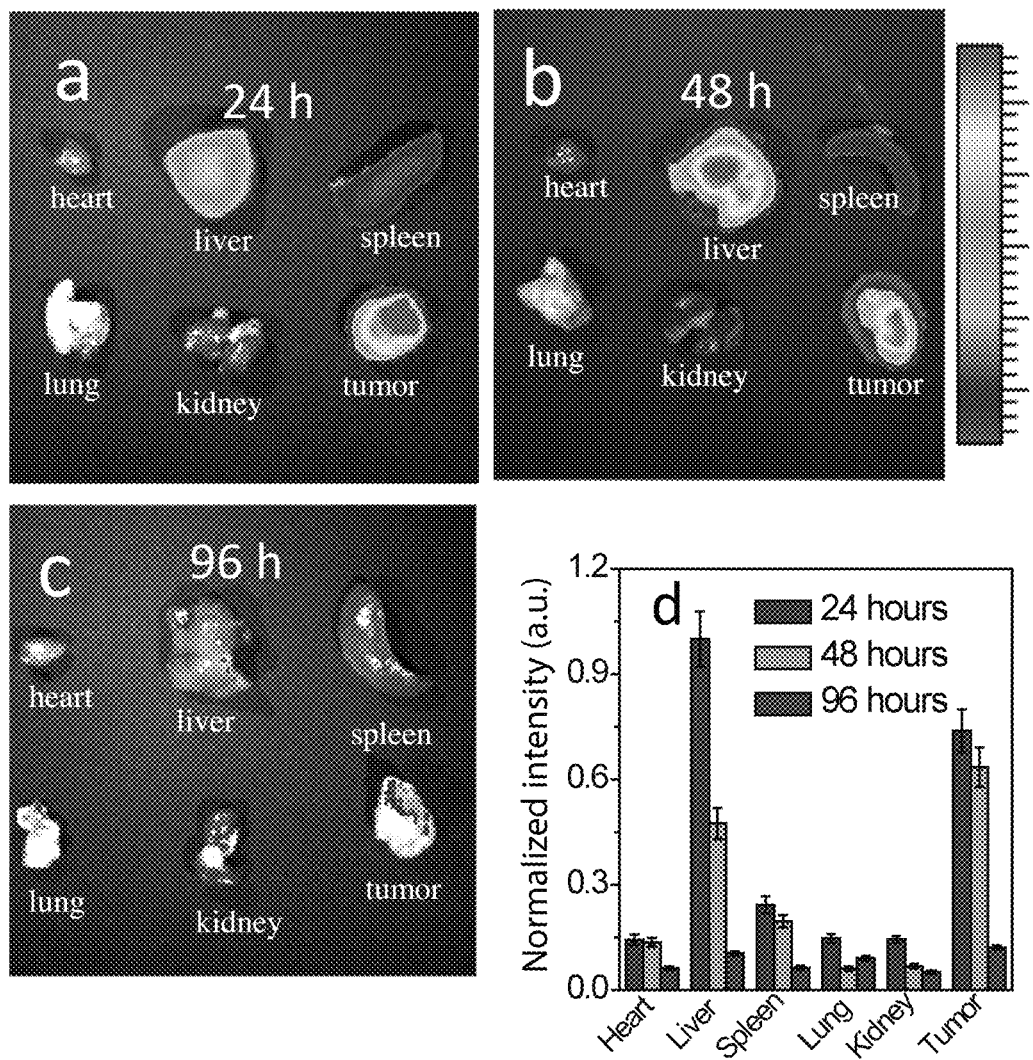
FIG. 28. In vivo distribution and biosafety of Car-BDP-TNM (50 μg mL$^{-1}$, 150 L). (a-c) Time dependent ex vivo MR fluorescence in major mice organs (heart, liver, spleen, lung, kidney, tumor). (a) After injection Car-BDP-TNM 24 h. (b) After injection Car-BDP-TNM 48 h. (c) After injection Car-BDP-TNM 96 h. (d) Normalized fluorescence intensity in mice organs, Values are the means±s.e.m. (n=3 mice per group).

The organ distribution of Car-BDP-TNM was evaluated by using ex vivo fluorescence imaging at predetermined time intervals (24, 48, and 96 h; FIG. 28). 24 h after treatment with the Car-BDP-TNM by intravenous injection, tumor and healthy organs including heart, liver, spleen, lung, and kidney were excised from tumor-bearing mice and imaged ex vivo. An intense MR fluorescence was seen in the excised tumor (FIG. 28), which indicates efficient Car-BDP-TNM accumulation in the tumor and less localization in healthy organs. After 48 h, the fluorescence from the liver and the tumor reduced. By 96 h, the fluorescence of the liver and the tumor had significantly weakened. The fluorescence from the major organs matched that from the fluorescence imaging of living mice (FIG. 26). Also quantified was the fluorescence intensity of the tumor and each organ from the Car-BDP-TNM-treated group at different time periods. The fluorescence intensity of the tumor was higher than that in healthy organs except the liver at 24 h (FIG. 28d). However, after 48 h, the fluorescence from the liver was reduced by half, but that from the tumor only reduced by 10%. At 96 h, the fluorescence from the liver could hardly be observed. A possible reason for this result might be that Car-BDP-TNM is mainly eliminated by macrophage cells in liver and spleen.

Figure 29:
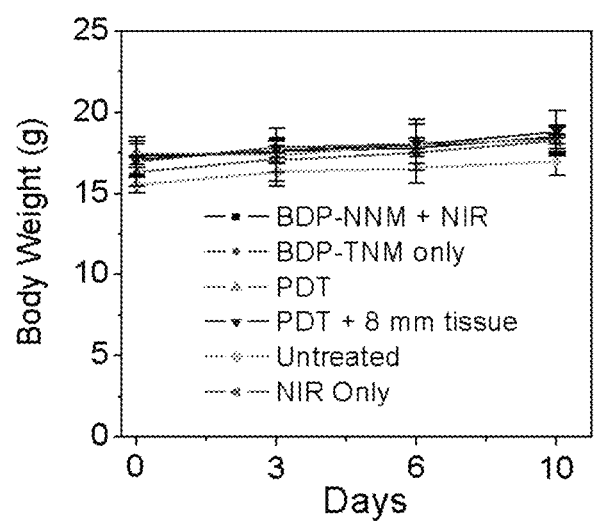
FIG. 29. Body weight changes with time of Balb/c mice under different treatments. Error bars indicate standard deviations; N=5.
Figure 30:
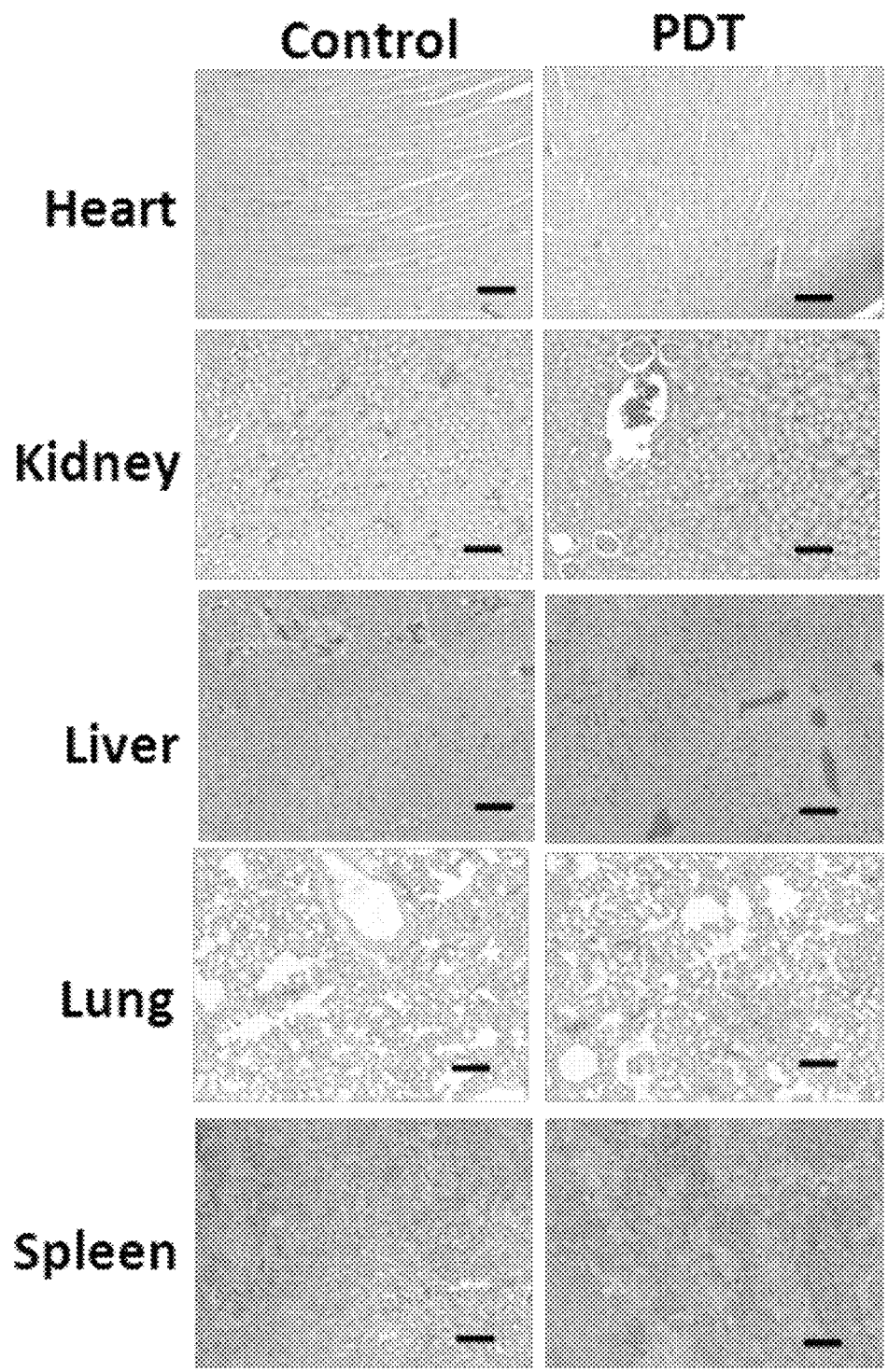
FIG. 30. H&E staining images of major organs (heart, liver, spleen, lung, kidney) of 4T1 tumor bearing mice in PBS group (control) and the Car-BDP-TNM with irradiation (PDT group), scale bar represents 100 μm.
Figure 31:
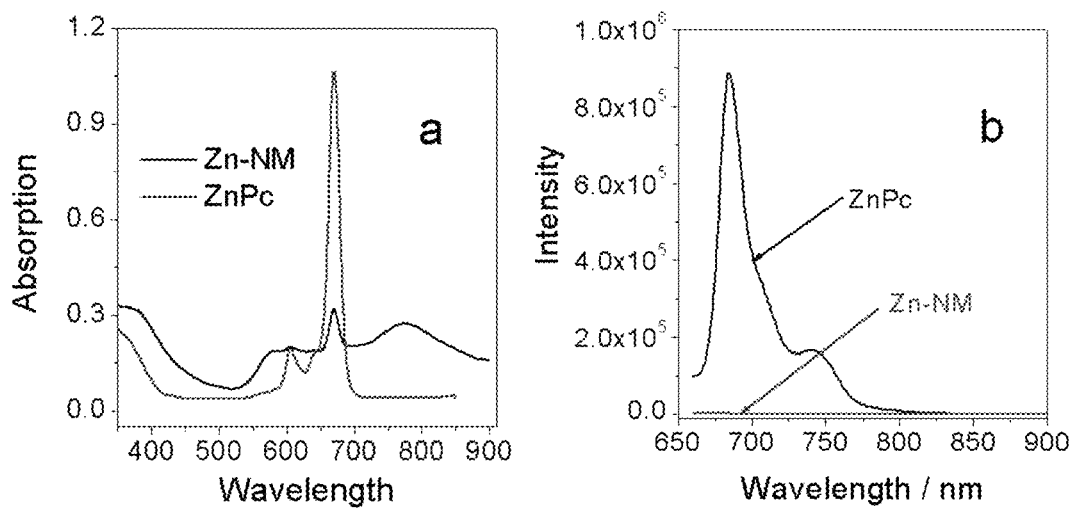
FIG. 31. (a) UV-Vis absorption of ZnPc in DMSO and Zn-NM in PBS; (b) fluorescence spectra of ZnPc in DMSO and ZnPc-NM in PBS, excited at 660 nm, (c=1.0×10$^{-5}$M, 22° C.). Zinc phthalocyanine (ZnPc), ZnPc-NM is a ZnPc nanomicelle.
Figure 39:
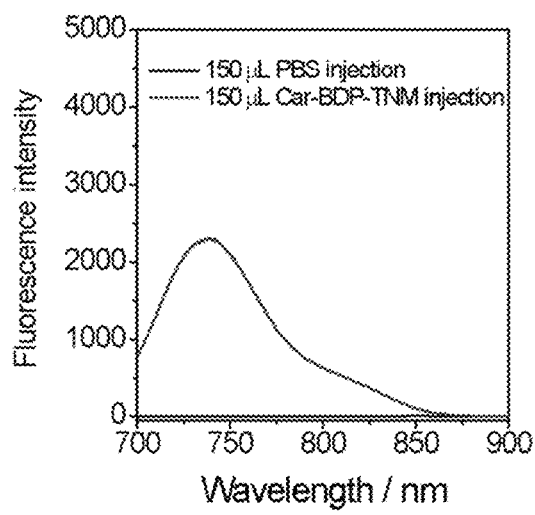
FIG. 39. Fluorescence spectra of post i.v. Car-BDP-TNM mice stool extracted solution, $\lambda_{ex}$=670 nm.

Potential in vivo toxicity is a great concern in the development of PDT reagents. Besides measuring body weights of mice in each cohort (FIG. 29), the H&E stained images of major organs (heart, liver, spleen, lung, and kidney) were also collected from healthy mice and those treated with Car-BDP-TNM as well as irradiation (FIG. 30). Neither noticeable organ damage nor inflammation lesions can be observed in the irradiated, treated group, by comparison with the healthy mice, which indicates that no obvious heart, liver, spleen, lung, or kidney dysfunctions of the mice were induced by the PDT process using Car-BDP-TNM. Further, the serum analysis experiment has been performed according to the reported protocol. (Song, G.; Liang, C.; Yi, X.; Zhao, Q.; Cheng, L.; Yang, K.; Liu, Z. *Adv. Mater* 2016, 28, 2716; Song, G.; Hao, J.; Liang, C.; Liu, T.; Gao, M.; Cheng, L.; Hu, J.; Liu, Z. *Angew. Chem. Int. Ed.* 2016, 55, 2122.) As shown in Table 2, abnormal results was not observed from this serum analysis, indicating that no observable inflammation was induced. In addition, excrement from the mice were collected 96 hours after the nanoparticle i.v. injection. Such excrement was dissolved in water and then extracted using dichloromethane. The fluorescence spectra of the extractions were subsequently tested. Compared to the PBS-injected control group, the fluorescence of Car-BDP was detected in excrement in the nanoparticle treated group (FIG. 39), indicating that Car-BDP-TNM was cleared from the body. All these results demonstrate that the as-designed Car-BDP-TNM possesses high biosafety and is highly biocompatible.

TABLE 2

Blood biochemistry and complete blood panel analysis of mice

| | Normal range | Control | 1 h | 3 h | 6 h | 12 h | 24 h | 48 h | 96 h | 168 h | 350 h |
|---|---|---|---|---|---|---|---|---|---|---|---|
| WBC (K/μL) | 1.8-10.7 | 6.4 | 6.4 | 7.6 | 5.8 | 6.2 | 6.4 | 7.4 | 6.8 | 4.8 | 4.5 |
| NE (K/μL) | 0.1-2.4 | 0.6 | 1.5 | 0.8 | 1.4 | 0.8 | 0.7 | 1.1 | 1.2 | 0.8 | 0.67 |
| LY (K/μL) | 0.9-9.3 | 4.7 | 4.4 | 5.7 | 4.9 | 4.8 | 6.0 | 5.9 | 5.3 | 3.71 | 3.72 |
| MO (K/μL) | 0.0-0.4 | 0.2 | 0.3 | 0.3 | 0.2 | 0.3 | 0.2 | 0.2 | 0.3 | 0.2 | 0.06 |
| EO (K/μL) | 0.0-0.2 | 0.1 | 0.1 | 0.1 | 0.1 | 0.1 | 0.1 | 0.1 | 0.1 | 0.1 | 0.05 |
| BA (K/μL) | 0.0-0.2 | 0.1 | 0.1 | 0.1 | 0.0 | 0.1 | 0.1 | 0.0 | 0.05 | 0.0 | 0.01 |
| RBC (M/μL) | 6.36-9.42 | 8.8 | 8.9 | 8.9 | 7.0 | 8.7 | 8.8 | 9.75 | 8.7 | 7.6 | 8.57 |
| HGB (g/dL) | 11.0-15.1 | 13.0 | 14.0 | 14.0 | 9.0 | 13.0 | 13.0 | 12.0 | 12.8 | 12.6 | 14.2 |
| HCT (%) | 35.1-45.4 | 38.0 | 39.5 | 41.2 | 38.0 | 43.0 | 39.5 | 36.8 | 40.4 | 39.9 | 44.5 |
| MCV (fL) | 45.4-60.3 | 49.1 | 49.8 | 49.8 | 49.8 | 49.3 | 48.6 | 46.0 | 52.0 | 52.5 | 51.9 |
| MCH (pg) | 14.1-19.3 | 17.3 | 15.1 | 16.2 | 18.1 | 14.9 | 15.8 | 18.8 | 16.5 | 16.6 | 16.6 |
| MCHC (K/μL) | 30.2-34.2 | 32.1 | 30.6 | 32.5 | 31.9 | 31.2 | 31.5 | 30.9 | 31.7 | 31.6 | 31.9 |

TABLE 2-continued

Blood biochemistry and complete blood panel analysis of mice

|  | Normal range | Control | 1 h | 3 h | 6 h | 12 h | 24 h | 48 h | 96 h | 168 h | 350 h |
|---|---|---|---|---|---|---|---|---|---|---|---|
| RDW (K/µL) | 12.4-27.0 | 18.6 | 21.7 | 19.9 | 24.9 | 20.1 | 28.7 | 22.3 | 21.5 | 21.9 | 20.6 |
| PLT (K/µL) | 592-2972 | 630 | 860 | 700 | 690 | 860 | 780 | 910 | 771 | 725 | 743 |
| MPV (fL) | 5.0-20.0 | 12.6 | 7.9 | 10.5 | 9.8 | 7.9 | 8.3 | 7.6 | 7.6 | 6.9 | 6.5 |

White blood cell (WBC), Neutrophils (NE), Lymphocytes (LY), Monocytes (MO), Eosinophils (EO), Basophils (BA), Red blood cell (RBC), Hemoglobin (HGB), Hematocrit (HCT), Mean corpuscular volume (MCV), Mean corpuscular hemoglobin (MCH), Mean corpuscular hemoglobin concentration (MCHC), Red blood cell distribution width (RDW), Platelet Thrombocyte (PLT), Mean platelet volume (MPV).

Figure 38:
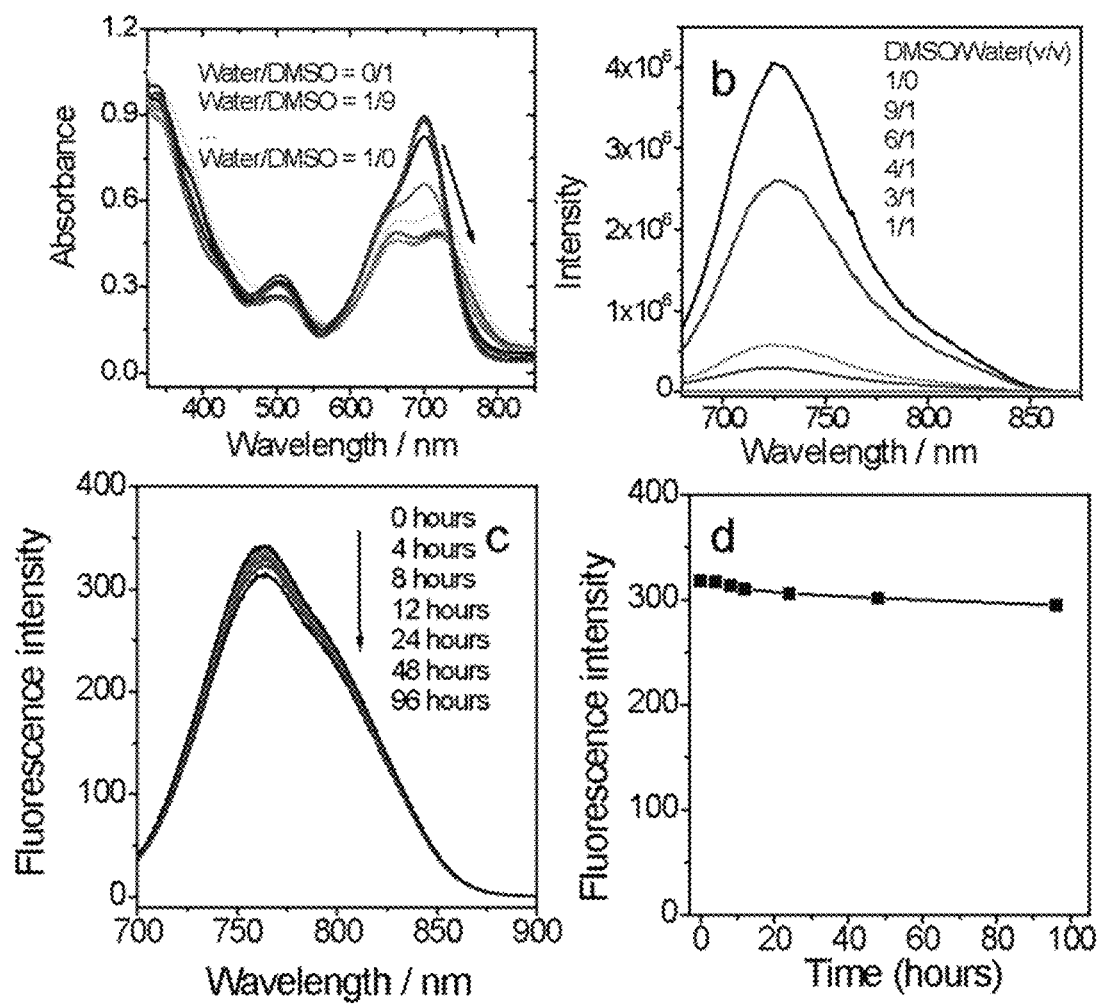
FIG. 38. (a) UV-vis absorption of Car-BDP in different volume water; (b) Fluorescence spectra of Car-BDP in different volume water, $\lambda_{ex}$=670 nm; (c) Fluorescence spectra of Car-BDP-TNM in serum (10%) cell medium, $\lambda_{ex}$=670 nm. (d) The change of fluorescence peak at 770 nm in different time.
Figure 40:
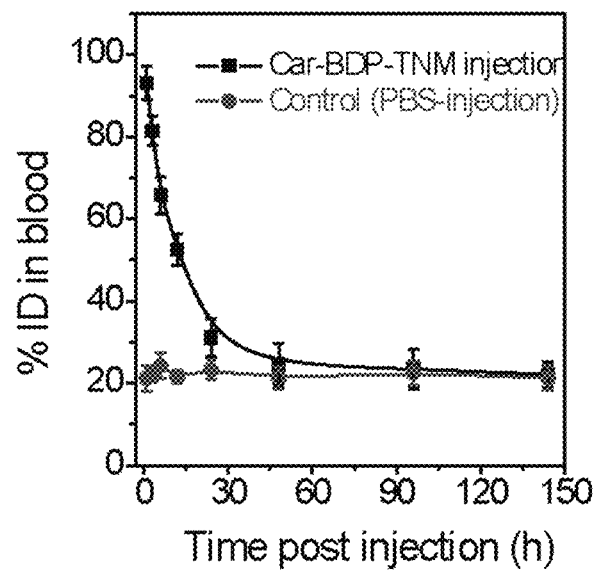
FIG. 40. Car-BDP-TNM circulation time curve (n=3 mice).
Figure 41:
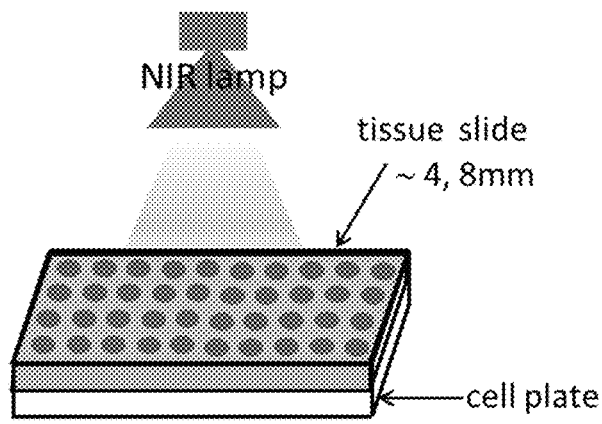
FIG. 41. Schematic illustration of Car-BDP-TNM mediated deep tissue PDT in vitro.
Figure 42:
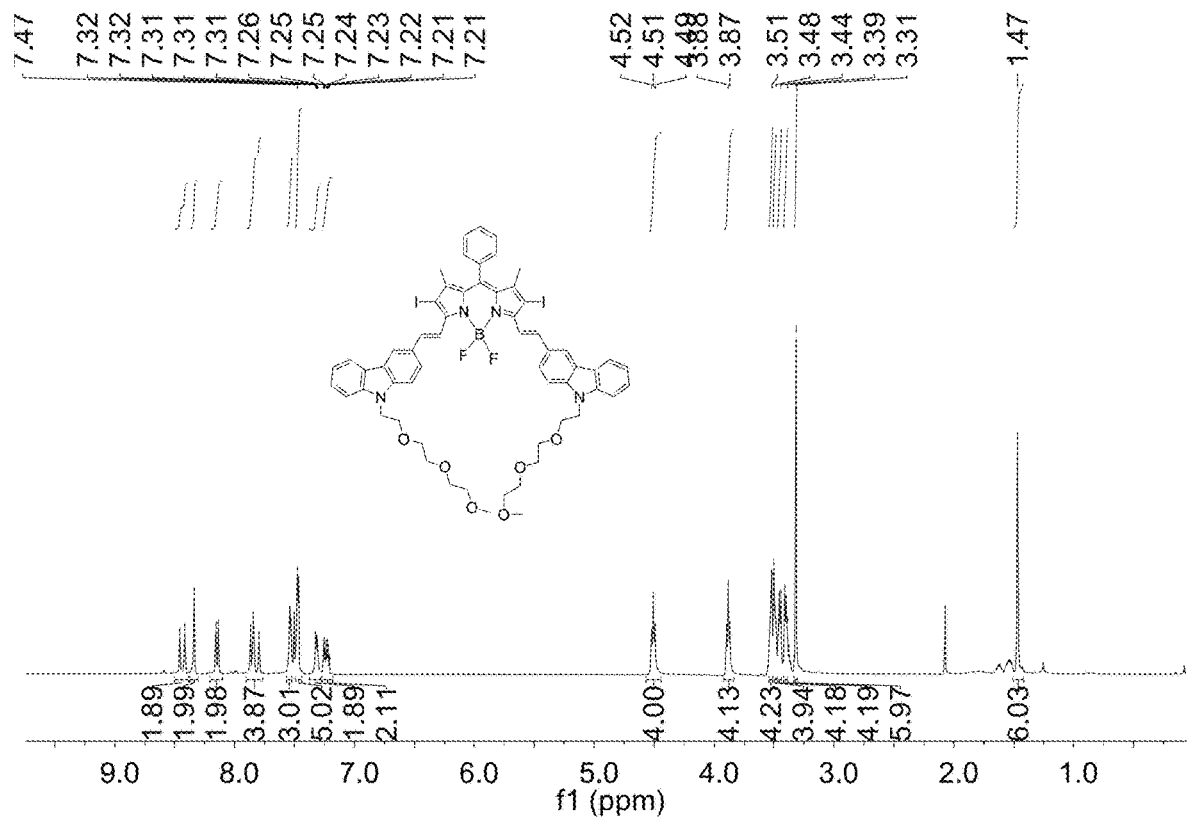
FIG. 42. $^1$H NMR of Car-BDP (400 Hz, CDCl$_3$).
Figure 43:
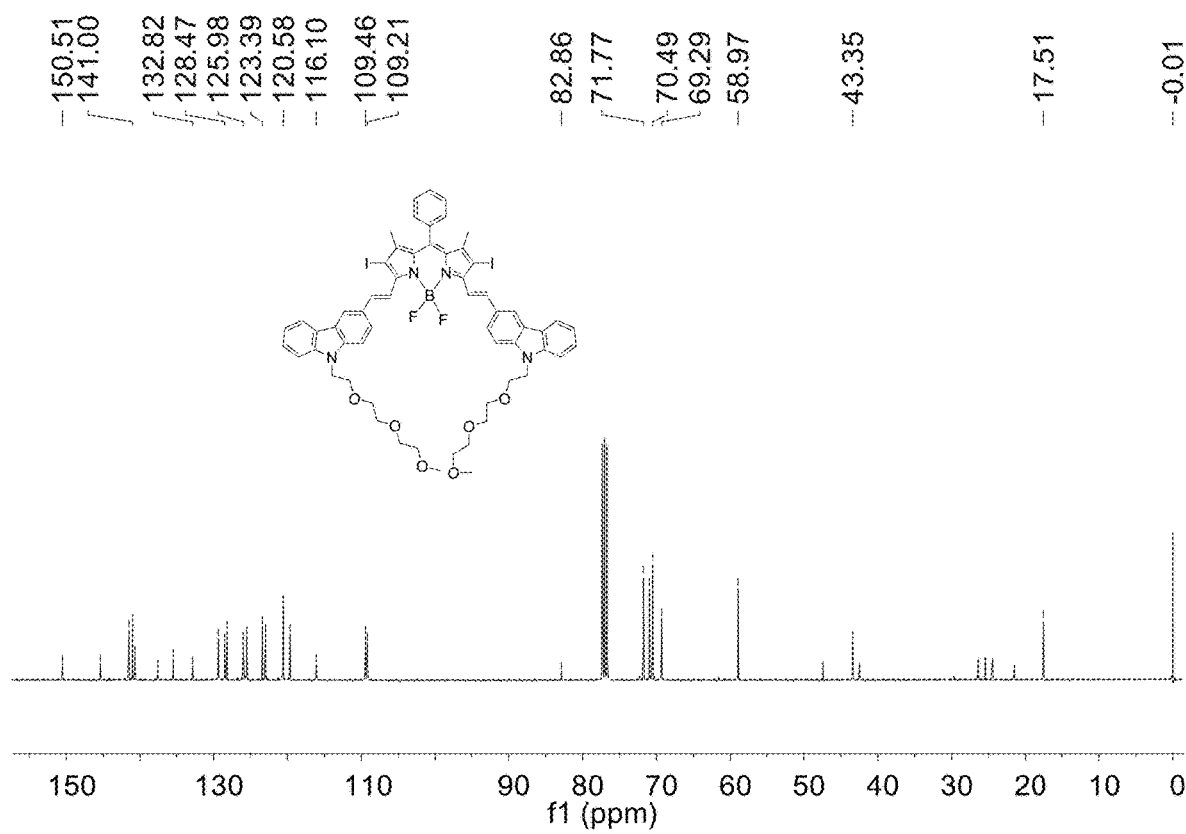
FIG. 43. $^{13}$C NMR of Car-BDP (400 Hz, CDCl$_3$).

Moreover, the stability and blood circulation of nanoparticles were evaluated. Since it was found that without polymer coating, the fluorescence of the hydrophobic Car-BDP molecule was sensitive to water molecules and was found to be gradually quenched as the amount of water increased; here this point was utilized as an approach and first used 10% FBS serum containing cell culture medium to simulate in vivo conditions. As a result, the fluorescence of Car-BDP-TNM remains over 96 hours (FIG. 38), indicating Car-BDP-TNM is stable under this condition. Moreover, the circulation time measurement of Car-BDP-TNM in vivo was conducted (FIG. 40). From the circulation time result, the fluorescence of Car-BDP-TNM was able to be detected for more than 90 hours, which also indicates Car-BDP-TNM has long in vivo stability and blood circulation.

Disclosed herein a new photosensitizer, a carbazole substituted BODIPY (Car-BDP), which shows remarkably intense absorption and high singlet oxygen quantum yield in the MR region. PLA-PEG-FA coated Car-BDP can form stable, small, biocompatible, organic nanoparticles (Car-BDP-TNM) that are biocompatible and capable of targeting tumor with specificity. Rather than using typically used laser light, with the a cost-effective ultralow power lamp light, Car-BDP-TNM has demonstrated exceptionally potent tumor volume inhibition efficiency (~80%) in deep tissue level in vivo. This cost-effective light source solution would be particularly important in developing countries where medical supplies are lacking. In addition, Moreover, the fluorescence of Car-BDP-TNM can be used to noninvasively guide PDT and monitor the results. Thus, the two-in-one MR PDT/imaging biodegradable organic nanoparticles are promising therapeutic and diagnostic candidates for cancer treatment. The photosensitizer may also pave the way for their uses in treating deep-tissue cancer, such as brain cancer or the peritoneal metastasis of ovarian cancer, especially in situations not accessible to regular cancer treatment.

In one aspect, the invention generally relates to a compound having the structural formula:

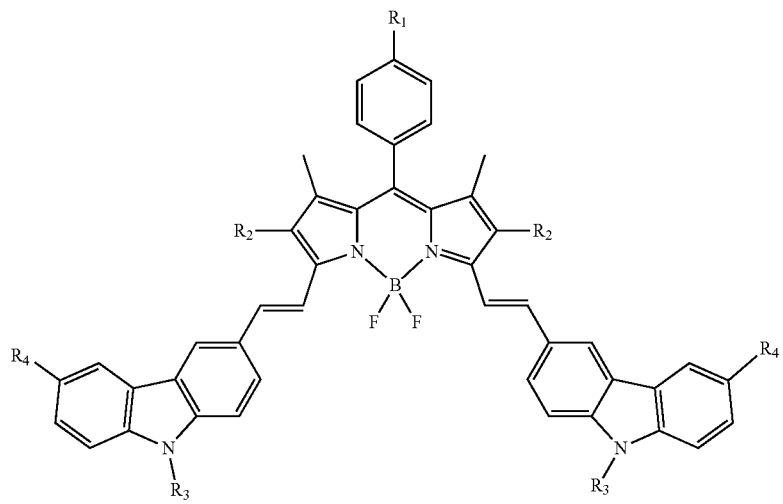

wherein $R_1$ is selected from the group consisting of H, Br, I, alkynyl, alkyl, alkenyl, azide, PEG, amine, carboxyl acid, and hydroxyl groups;

each $R_2$ is independently selected from Br and I;

each $R_3$ is independently selected from the group consisting of alkynyl, alkyl, alkenyl, azide, PEG, amine, carboxylic acid, and hydroxyl groups; and each $R_4$ is independently selected from the group consisting of H, Br, I, phenyl, and phenylethynyl groups, or a pharmaceutically acceptable form thereof.

In certain preferred embodiments, $R_1$ is a H, Br, I, —OH, or a $C_1$-$C_6$ alkyl group.

In certain preferred embodiments, each $R_3$ is —($C_2H_5$—O)$_k$—, wherein k is an integer from about 1 to about 700 (e.g., from about 1 to about 700, from about 1 to about 500, from about 1 to about 300, from about 1 to about 100, from about 1 to about 50, from about 10 to about 700, from about 50 to about 700, from about 100 to about 700, from about 5 to about 500, from about 10 to about 300).

In certain preferred embodiments, each of $R_1$ and $R_4$ is H, and each $R_2$ is I.

In another aspect, the invention generally relates to a nanoparticulate material. The nanoparticulate material includes: a biodegradable amphiphilic polymer nanomicelle; and a compound having the structural formula:

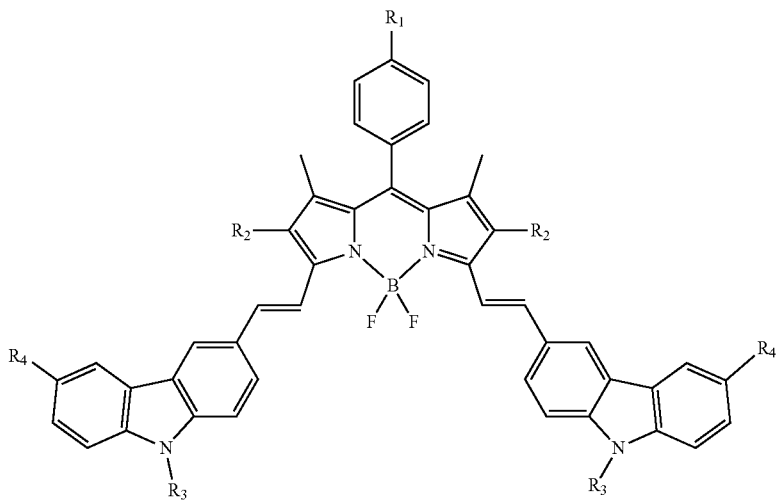

wherein $R_1$ is selected from the group consisting of H, Br, I, alkynyl, alkyl, alkenyl, azide, PEG, amine, carboxyl acid, and hydroxyl groups;

each $R_2$ is independently selected from Br and I;

each $R_3$ is independently selected from the group consisting of alkynyl, alkyl, alkenyl, azide, PEG, amine, carboxylic acid, and hydroxyl groups;

each $R_4$ is independently selected from the group consisting of H, Br, I, phenyl, and phenylethynyl groups, or a pharmaceutically acceptable form thereof.

The compound is encapsulated in the biodegradable polymer nanomicelle.

In certain embodiment, the biodegradable amphiphilic polymer nanomicelle is adapted to preferential cellular uptake by tumor cells.

In certain embodiment, the biodegradable amphiphilic polymer comprises folic acid. In certain embodiment, the biodegradable amphiphilic polymer comprises a tumor cell targeting peptide or antibody moiety.

In certain embodiment, the biodegradable amphiphilic polymer comprises a co-polymer of PLA-PEG-FA.

In certain embodiment, the biodegradable amphiphilic polymer is

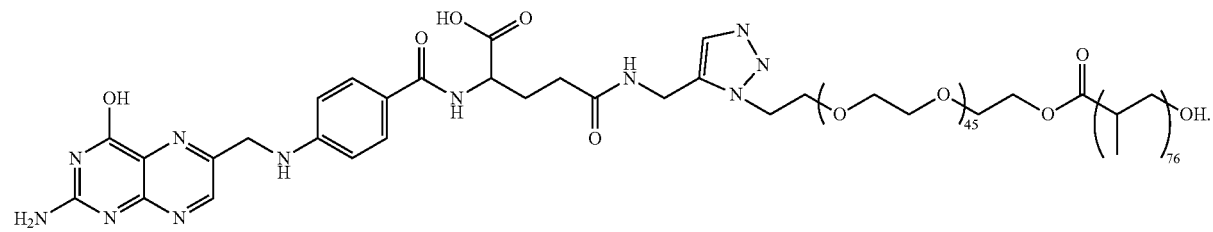

PLA-PEG-FA

In certain preferred embodiment, the compound is

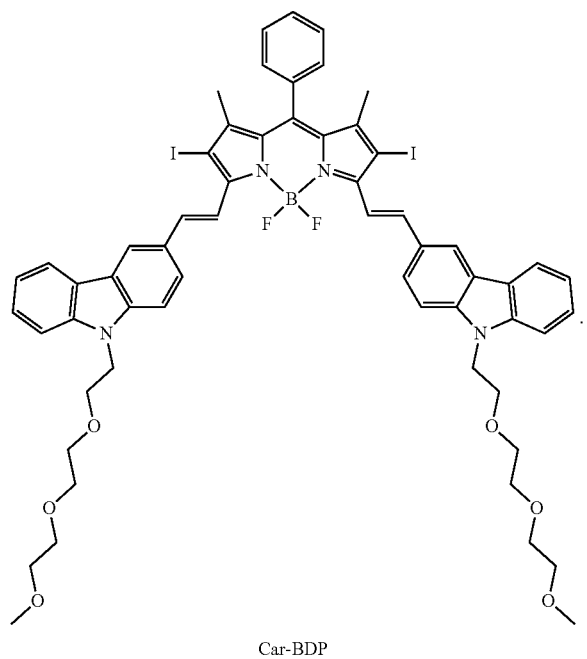

Car-BDP

In yet another aspect, the invention generally relates to a pharmaceutical composition comprising a compound disclosed herein in an amount effective to treat, prevent, or reduce one or more diseases or disorders, in a mammal, including a human, and a pharmaceutically acceptable excipient, carrier, or diluent.

In yet another aspect, the invention generally relates to a nanoparticulate material disclosed herein in an amount effective to treat, prevent, or reduce one or more diseases or disorders, in a mammal, including a human, and a pharmaceutically acceptable excipient, carrier, or diluent.

In yet another aspect, the invention generally relates to a method for treating a cancer or tumor. The method includes: administering to a subject in need thereof a nanoparticulate material comprising a photosensitizer and a targeting moiety, wherein the photosensitizer is sensitive to excitation in the range of about 600 nm to about 1,000 nm and the targeting moiety has an affinity to a cancer or tumor cell or is preferentially upkate by a cancer or tumor cell; and directing a light beam at a location of the cancer or tumor, wherein the lightbeam comprises a wavelength from about 600 nm to about 1,000 nm.

In certain preferred embodiment, the photosensitizer comprises a compound having the structural formula:

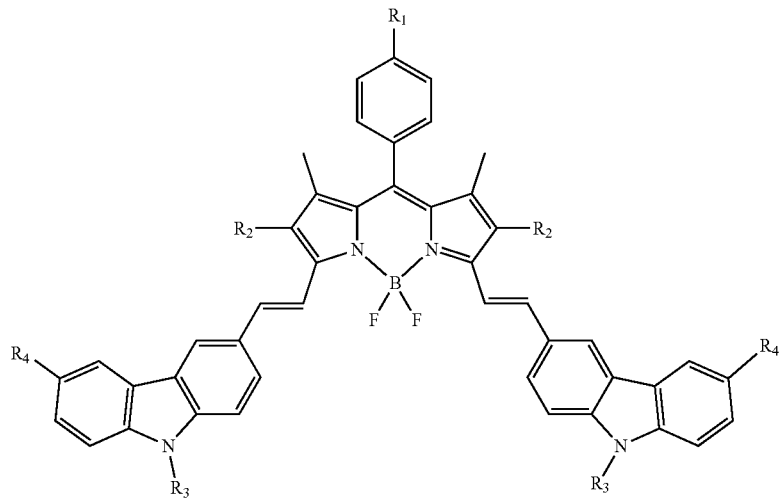

wherein
$R_1$ is selected from the group consisting of H, Br, I, alkynyl, alkyl, alkenyl, azide, PEG, amine, carboxyl acid, and hydroxyl groups;
each $R_2$ is independently selected from Br and I;
each $R_3$ is independently selected from the group consisting of alkynyl, alkyl, alkenyl, azide, PEG, amine, carboxylic acid, and hydroxyl groups; and
each $R_4$ is independently selected from the group consisting of H, Br, I, phenyl, and phenylethynyl groups.

Any suitable targeting moiety may be employed. In certain embodiments, the targeting moiety is a folic acid group. In certain embodiment, the targeting comprises a tumor cell targeting peptide or antibody moiety.

Any suitable light source may be used to provide the excitation light. In certain embodiments, the photosensitizer is sensitive to excitation in the about 600 nm to about 1,000 nm range (e.g., about 600 nm to about 900 nm, about 600 nm to about 800 nm, about 600 nm to about 700 nm, about 700 nm to about 1,000 nm, about 800 nm to about 1,000 nm, about 900 nm to about 1,000 nm).

In certain embodiments, the excitation light is from a coherent light source. In certain embodiments, the excitation light is from a non-coherent light source. In certain embodiments, the excitation light is from a halogen lamp. In certain embodiments, the lightbeam comprises a wavelength from about 600 nm to about 1,000 nm (e.g., about 600 nm to about 900 nm, about 600 nm to about 800 nm, about 600 nm to about 700 nm, about 700 nm to about 1,000 nm, about 800 nm to about 1,000 nm, about 900 nm to about 1,000 nm).

Compounds and methods disclosed herein afford high singlet-oxygen yield ($\Phi_A$), e.g., greater than about 40%, 50%, 60%, 70%, or 80%. In certain embodiments, the singlet-oxygen yield is from about 50% to about 70%. In certain embodiments, the singlet-oxygen yield is from about 70% to about 80%.

EXPERIMENTAL

Chemicals

ZnPc, 2,4-dimethylpyrrole, DPBF, PEG-2000, lactide, trifluorobonetherate ($BF_3 \cdot Et_2O$), 1,3-diphenylisobenzofuran (DPBF), 2,3-dichloro-5,6-dicyano-1,4-benzoquinone (DDQ), 3-(4,5-dimethylthiazol-2-yl)-2,5-diphenyltetrazolium bromide (MTT), 2',7'-dichlorofluorescein-diacetate (DCFH-DA), propidium iodide (PI), and folic acid (compound 6) were purchased from Sigma-Aldrich (St. Louis, Mo., USA). Dulbecco's Modified Eagle Medium (DMEM), fetal bovine serum (FBS), penicillin-streptomycin, trypsin-EDTA (EDTA=ethylenediaminetetraacetic acid), and Hank's balanced salt solution (HBSS) were obtained from Invitrogen (Carlsbad, Calif., USA). PEG3400-benzyl was purchased from Gelest, Inc. (Morrisville, Pa., USA). Ultra-pure water was prepared by using a Millipore Simplicity System (Millipore, Bedford, USA). All the above-mentioned chemicals were used as received without further purification.

Characterization $^1$H NMR spectra were recorded with a Bruker 400 MHz spectrometer. UV-Vis spectra were recorded on an Agilent Cary-5 spectrophotometer. Steady-state fluorescence spectra were measured on an Edinburgh Instrument FLS-920 spectrometer. The morphology of the Car-BDP-TNM, Car-BDP-NNM, and ZnPc nanoparticles were characterized by using a JEOL JEM-200CX transmission electron microscope (TEM) operated at 80 kV. The sample for TEM measurement was prepared by dropping the solution onto a carbon-coated copper grid following negative staining with 2.0% (w/v) phosphotungstic acid. The particle size and size distribution of Car-BDP-TNM, Car-BDP-NNM and ZnPc-NM were measured by using dynamic light scattering (DLS) on a Mastersizer 2000 particle size analyzer.

Synthesis of Car-BDP

To a solution of compound 2 (280 mg, 0.5 mmol) and compound 3 (700 mg, 2.22 mmol) in dry toluene (30 mL), acetic acid (1.5 mL) and piperidine (1.5 mL) were added under an $N_2$ atmosphere. The reaction mixture was heated at 135° C. under reflux with a Dean-Stark trap to remove the water generated by the condensation. The reaction was monitored by TLC (dichloromethane as eluent). After consumption of all the starting materials, the reaction mixture was cooled to room temperature (rt) and the majority of the solvent was evaporated under reduced pressure. Water (150 mL) was added to the residue and the product was extracted from $CH_2Cl_2$ (3×100 mL). The organic phase was dried over $Na_2SO_4$, the solvent was evaporated under reduced pressure, and the crude products thus obtained were purified by column chromatography (silica gel, $CH_2Cl_2$). The green band was collected to obtain a black solid. $^1$H-NMR (400 Hz, $CDCl_3$) δ=8.45 (d, 2H, J=16.0 Hz), 8.33 (s, 2H), 8.15 (d, 2H, J=8.0 Hz), 7.87-7.79 (m, 5H), 7.54-7.53 (m, 3H), 7.47-7.46 (m, 5H), 7.32-7.31 (m, 2H), 7.25-7.21 (m, 2H), 4.52-4.49 (m, 4H), 3.90-3.87 (m, 4H), 3.52-3.51 (m, 4H), 3.50-3.48 (m, 4H), 3.45-3.43 (m, 4H), 3.41-3.38 (m, 4H), 3.31 (s, 6H), 1.47 (s, 6H). $^{13}$C-NMR (100 Hz, $CDCl_3$) δ=150.5, 145.4, 141.5, 140.7, 137.6, 135.5, 132.8, 129.4, 128.5, 128.2, 125.9, 125.5, 123.4, 122.9, 120.6, 119.7, 116.1, 109.5, 109.2, 82.9, 71.8, 70.9, 70.6, 70.5, 69.3, 58.9, 43.4, 17.5 ppm.

Synthesis of Car-BDP-TNM

Car-BDP-TNM was prepared via self-assembly of Car-BDP, PEG2000-PLA39000, and PLA30000-PEG3400-FA with a single-step sonication method. Briefly, 1.0 mg Car-BDP, 40 mg PEG2000-PLA39000, and 10 mg PLA30000-PEG3400-FA were dissolved in 4 mL $CH_2Cl_2$. The mixture was added to 10 mL 0.5% F-127 solution and sonicated using an ultrasonic processor at 35 kHz and 250 W for 15 min. Afterward, the solution was kept stirring for 1 h with protection from light at room temperature. The remaining organic solvent was removed in a rotary evaporator at reduced pressure at 30° C. for 4.0 h. Finally, the Car-BDP-TNM was centrifuged at 9000×g for 60 min. Large nanoparticles precipitated and the supernatant containing small nanoparticles was decanted and stored at 4° C. until use. Similar procedures were used to prepare the Car-BDP-NNM and ZnPc-NM.

Loading Percentage of Photosensitizes (Car-BDP) in Nanoparticles

Photosensitizers encapsulated within the PLA-PEG were characterized for their loading percentage as follows: Firstly, 1.0 mg Car-BDP was dissolved in 100 mL DMF, and the absorption spectra was recorded. The precipitated Car-BDP-TNM was also dissolved in 100 mL DMF and the absorption spectra measured. The difference in absorption peak of Car-BDP "before" and "after" loading gives the mass of photosensitizers that was incorporated into the nanoparticles and can be calculated based on the standard curve created from the absorption spectra of standard B-1 solutions. The photosensitizer loading percentage can then be derived by using the following formula:

Photosensitizer loading (%)=Mass of photosensitizers incorporated into nanoparticles/Mass of nanoparticles.

Photostability of Car-BDP-TNM in PBS Buffer

50 μg mL$^{-1}$ Car-BDP-TNM was irradiated with MR light (670-800 nm). The MR light was obtained from a halogen lamp and a band pass filter (670-800 nm, 12 mW cm$^{-2}$). The fluorescence emission of Car-BDP-TNM was measured at different times by using a fluorescence spectrometer.

Detection of Production of $^1O_2$ in Solution

In a typical experiment, 50 μg of the Car-BDP-TNM, Car-BDP-NNM was suspended in 1 mL of PBS (equilibrated with air at RT) containing 10 μM of singlet oxygen sensor green (SOSG) dye, which is a singlet oxygen inductor. The mixture was then placed in a cuvette and the solution was irradiated at 670-800 nm of a halogen lamp, 12 mW cm$^{-2}$ for 5 min, with the fluorescence emission of SOSG (upon excitation at 470 nm) being measured between intervals using a fluorescence spectrophotometer.

Measurement Singlet Oxygen Quantum Yield ($\Phi_A$)

The $\Phi_A$ quantum yields were calculated by using methylene blue in dichloromethane with $\Phi_A$=0.52 as reference. The absorbance of the $^1O_2$ scavenger, 1,3-diphenylisobenzofuran (DPBF), was adjusted to around 1.0 in air-saturated DMF. Then the photosensitizer was added and its absorbance was adjusted to around 0.2-0.3. Then the cuvette was exposed to monochromatic light (710 nm) from the fluorimeter at the peak absorption wavelength for 20 s. The slope of the absorbance maxima of DPBF at 415 nm versus time graph was calculated for each photosensitizer. The singlet oxygen quantum yields ($\Phi_A$) were calculated according to equation (1)

$$\Phi_A = \Phi_{(MB)} \times k_{(Car-BDP)} \times F_{(MB)} / k_{(MB)} \times F_{(Car-BDP)} \quad (1)$$

k is the slope of the difference in the change in the absorbance of DPBF (414 nm) with irradiation time, and F is the absorption correction factor, which is given by $F=1-10^{OD}$ (OD at the irradiation wavelength).

Cell Culture

HeLa cell line (cervical cancer cells), 4T1 (breast cancer Cells), and Greengo cell lines (skin epidermal cells) were obtained from American Type Culture Collection (ATCC, Manassas, Va., USA) and grown in DMEM culture medium supplemented with 10% FBS, 100 units $mL^{-1}$ of penicillin and 100 μg $mL^{-1}$ of streptomycin, and maintained in a humidified, 5% carbon dioxide ($CO_2$) atmosphere at 37° C.

Uptake of Car-BDP-TNM and Car-BDP-NNM into Cells

HeLa cells (60000 cells/$cm^{-2}$) were plated onto appropriate culture plates. After 4 h, 50 g $mL^{-1}$ nanoparticles were added and the cells were incubated for 12 h at 37° C. in a humidified, 5% $CO_2$ atmosphere, after which the old culture medium containing unbound and noninternalized nanoparticles was discarded and the cells were washed twice with PBS being replaced with fresh culture medium. Laser scanning confocal fluorescence microscopy was used to observe the fluorescence of nanomicelles. Excitation wavelength was 633 nm. Capture wavelength region was 700-800 nm.

Cell Viability Assay

Cell viability was verified by MTT assay. HeLa, 4T1, and Greengo cell lines were used. Firstly, the cells (200 L, 5000) were plated in a 96-well plate. After 12 h, the nanoparticles were added at different concentrations (0, 5, 10, 15, 20, 25 g $mL^{-1}$). The nanoparticles were taken up over 5 h. The cells were irradiated with MR light (670-800 nm, 12 mW $cm^{-2}$) with a halogen lamp as the light source. After 30 min irradiation, the cells were incubated another 12 h under 5% $CO_2$ atmosphere at 37° C. MTT solution (5.0 mg $mL^{-1}$, 50 L) was added to every well and left for 4 h. The old cell culture medium was removed carefully and 200 L DMSO was added to every well. A microplate reader (Bio-Rad) was used to record the absorption at 595 nm.

Cell viability (%)=the absorption of irradiation group/the absorption of dark group ROS Detection in Live Cells ROS generated in cells treated with PDT were detected immediately after the photosensitization experiments by using a singlet oxygen indictor. Briefly, the culture medium of cells that was exposed to the respective Car-BDP-TNM (10 μg $mL^{-1}$) was first replaced with HBSS containing 25 μM 2', 7'-dichlorodihydrofluorescein diacetate ($H_2DCFDA$) that sufficiently covered the adhering cells. The cells were then subjected to photosensitization by using 670-800 nm MR lamp light irradiation for 10 min. After irradiation, the HBSS buffer was removed carefully and the cells washed with HBSS buffer three times. Immediately after that, fluorescent images of carboxy-$H_2DCFDA$, staining on the cells were promptly captured by excitation at 488 nm using a fluorescence microscope (Nikon, Tokyo, Japan).

Dead Cells Detection in PDT

The cells ($1\times10^5$) per well were seeded on six-well plates and incubated in complete medium for 24 h at 37° C. The medium was then replaced with fresh culture medium containing Car-BDP-TNM (25 μg $mL^{-1}$) to incubate for 4 h at 37° C. The cells were irradiated with a 670-800 nm near infrared light at a power of 12 mW $cm^{-2}$ for 10 min. Afterward, the cells were stained with propidium iodide (PI) according to the manufacturer's instruction. After 5 min, the PI solution was removed and PBS used to wash cells at least three times. The dead cells were visualized with a fluorescence microscopy. Excitation wavelength was 514 nm. Emission detection wavelength region was 580-620 nm.

Targeted PDT on Subcutaneous Breast Tumor Model

Tumor-targeting property of Car-BDP-TNM and Car-BDP-NNM was studied in 4T1 tumor-bearing mice. They were subjected to the following treatments: group 1, intravenous injection of Car-BDP-TNM; group 2, intravenous injection of Car-BDP-NNM. 150 μL, 50 μg $mL^{-1}$ Car-BDP-TNM, or Car-BDP-NNM in saline were intravenously injected. The fluorescence of Car-BDP-TNM and Car-BDP-NNM was measured at different time (6, 24, 48 h) with IVS animal imaging. Excitation filter was Cy5.5 (680-730 nm) and emission filter was ICG (750-850 nm)

In Vivo Bio-Distribution and Biosafety

Figure 32:
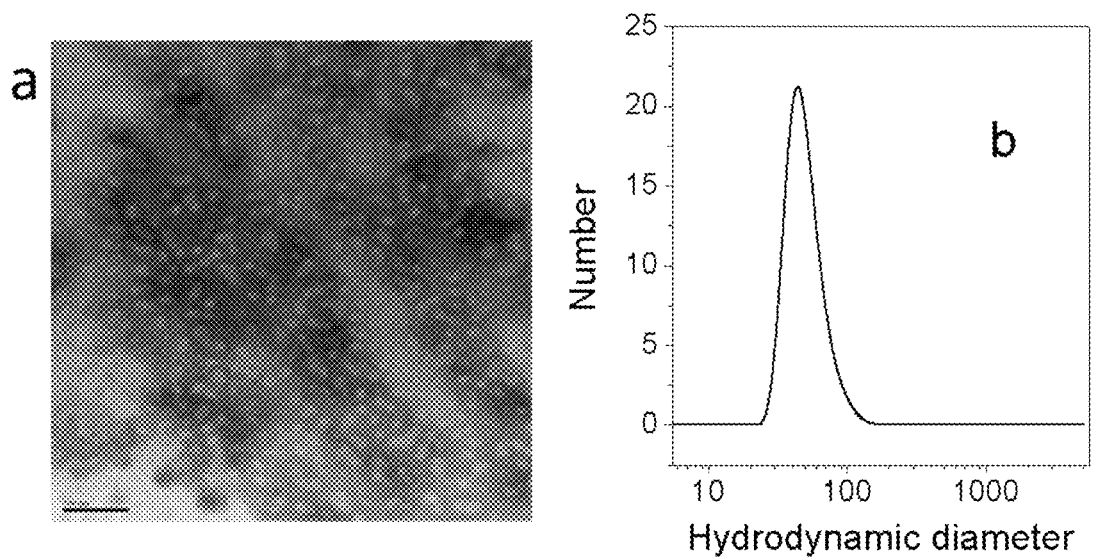
FIG. 32. (a) TEM image of ZnPc-NM stained by phosphotungstic acid, scale bar represents 100 nm. (b) Hydrodynamic diameter of ZnPc-NM in PBS.
Figure 33:
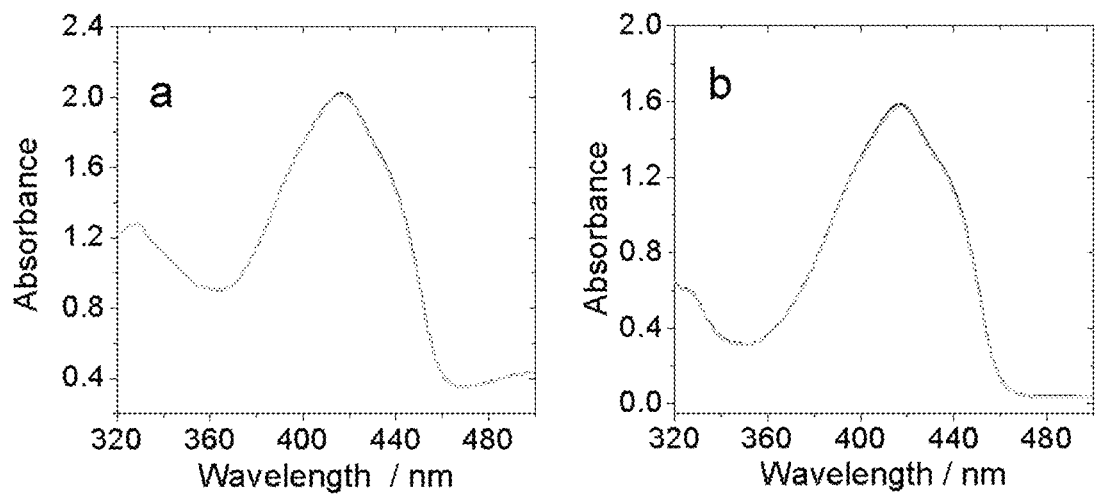
FIG. 33. UV-Vis spectra change of (a) Car-BDP (10 μM) and DPBF (10 μM) mixture and (b) DPBF (10 μM) in dark conditions over 120 s, recorded every 20 s.
Figure 34:
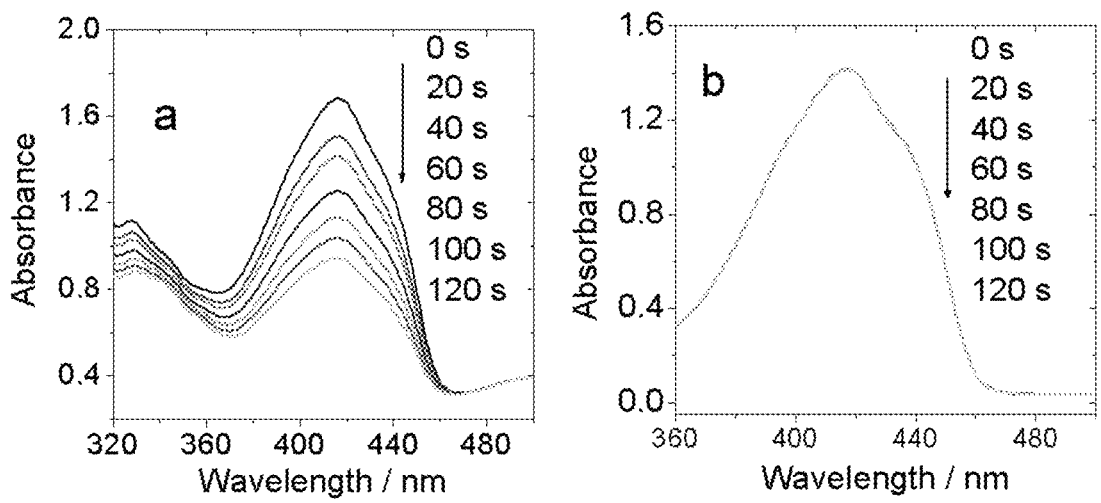
FIG. 34. UV-Vis spectral change of (a) Car-BDP-NNM and DPBF, (b) ZnPc-NM and DPBF under irradiation (670-800 nm, 12 mW cm$^{-2}$) over 120 s, recorded every 20 s.
Figure 35:
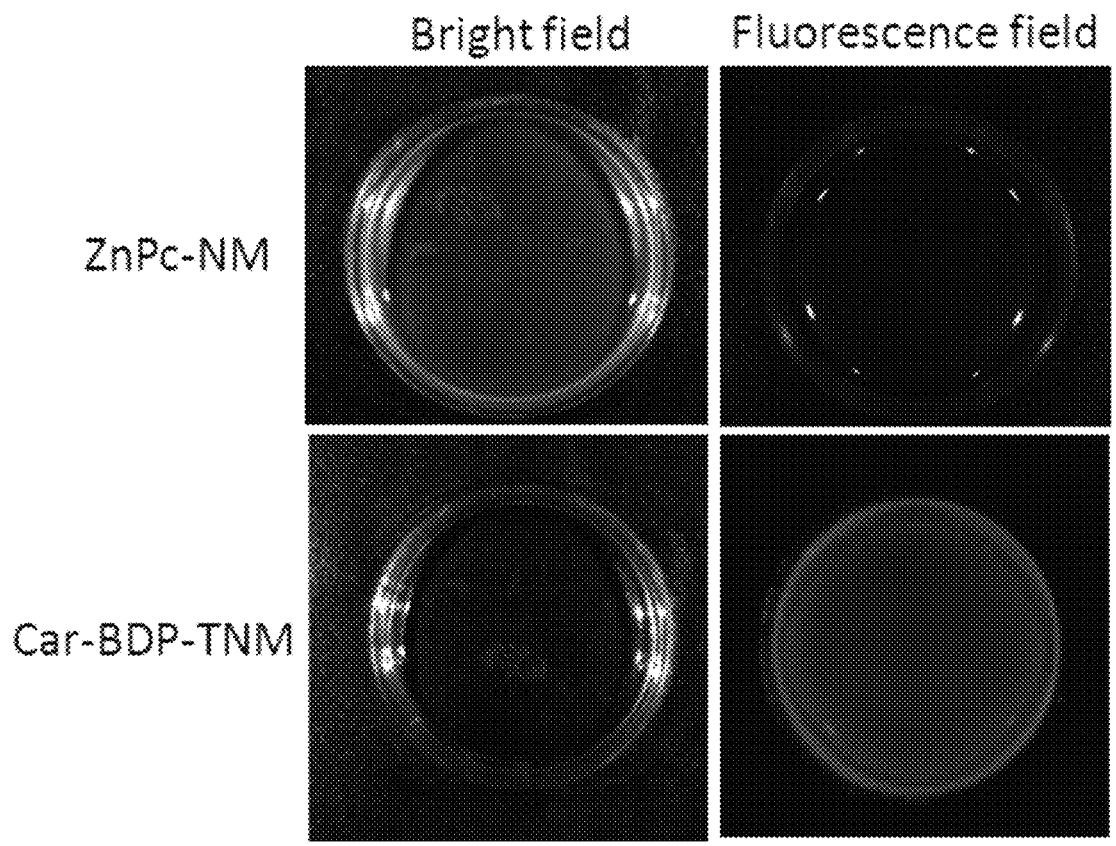
FIG. 35. Photograph with fluorescence emission of Car-BDP-TNM (25 μg mL) with caliper animal image instrument, $\lambda_{ex}$=720 nm (3 mW cm$^{-2}$), capture wavelength 730-850 nm, the red color is a pseudo color, exposure time is 50 ms.
Figure 36:
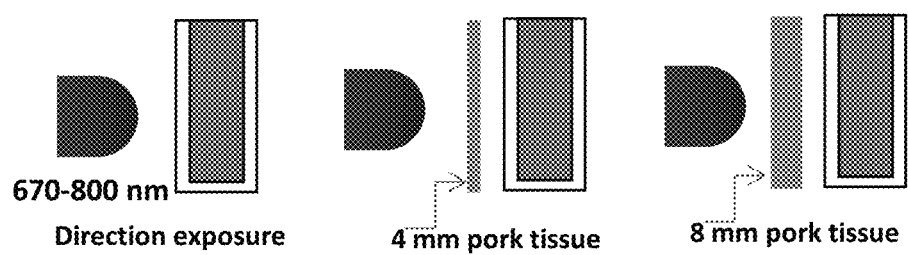
FIG. 36. A schematic illustration of experiment design, sample was blocked from light by pork slices of varied thicknesses.
Figure 37:
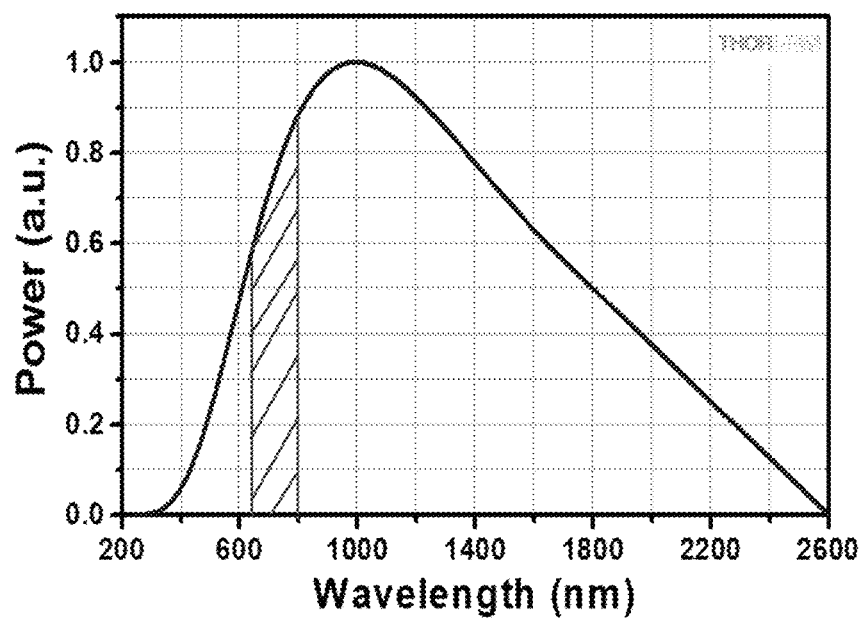
FIG. 37. Halogen lamp emission spectra, the red diagonal line region are the excitation source for PDT (670-800 nm).

The in vivo biodistribution of the Car-BDP-TNM in 4T1 tumor bearing mice was assessed by using IVS animal imaging system. After tail-vein injection of Car-BDP-TNM, mice were sacrificed, and major organs including heart, liver, spleen, lung, and kidney were carefully removed for visualization under the imaging system in different time periods (24, 48 h, and 96 h). The fluorescent signals of each organ were analyzed by the accompanied software (FIG. 30). (On the tenth day after intravenous of Car-BDP-TNM, mice were sacrificed major organs (heart, liver, spleen, lung, and kidney) were dissected for H&E staining (FIG. 32).

In Vivo Tumor Inhibition Assay

An in vivo phototoxicity assay was performed using 4T1 tumor-bearing mice. The mice were subjected to six different treatments: group 1, PBS; group 2, irradiation only; group 3, tail-vein injection of Car-BDP-TNM only; group 4, tail-vein injection of Car-BDP-NNM combined with $mL^{-1}$ light exposure; group 5, tail-vein injection of Car-BDP-TNM combined with MR light exposure; group 6, tail-vein injection of Car-BDP-TNM combined with exposure to infrared light that penetrated to a depth of 8.0 mm through tissue. Each group contained five mice. 150 μL of 50 μg nanoparticles in saline was injected by tail vein. 24 h later, halogen lamp treatment was performed on groups 2, 4, 5, 6 by irradiating the tumor region with a 670-800 nm lamp at 12 mW $cm^{-2}$ for 30 min. Two mice from each group were euthanized 10 d post-treatment, and tumor tissues of the above-mentioned treatment groups 1-6 were harvested for histological study by H&E staining under a BX51 optical microscope (Olympus, Japan) in a blinded fashion by a pathologist. Different treatment groups were monitored by measuring the tumor size using a Vernier caliper for 10 d after the PDT treatment. Tumor size=width×width×length/2.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:
1. A compound having the structural formula:

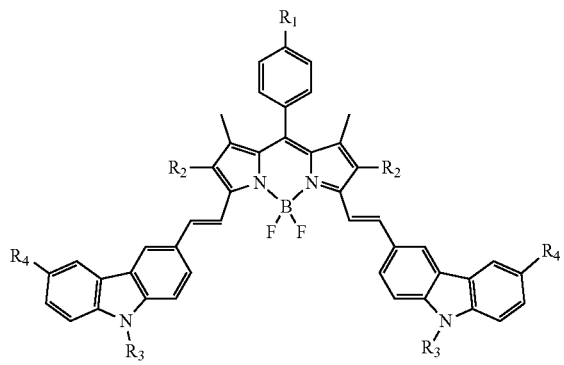

wherein
$R_1$ is selected from the group consisting of H, Br, I, alkynyl, alkyl, alkenyl, azide, PEG, amine, carboxyl acid, and hydroxyl groups;
each $R_2$ is independently selected from the group consisting of Br and I;
each $R_3$ is —$(C_2H_5$—$O)_k$—, wherein k is an integer from about 1 to about 700; and
each $R_4$ is independently selected from the group consisting of H, Br, I, phenyl, and phenylethynyl groups, or
a pharmaceutically acceptable form thereof.
2. A compound having the structural formula:

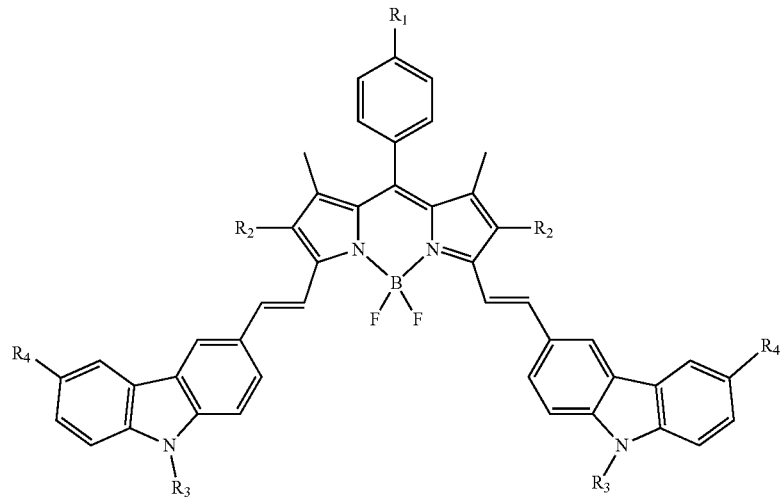

wherein
R₁ is H;
each R₂ is I;
each R₃ is independently selected from the group consisting of alkynyl, alkyl, alkenyl, azide, PEG, amine, carboxylic acid, and hydroxyl groups; and
each R₄ is H, or
a pharmaceutically acceptable form thereof.

3. A nanoparticulate material comprising:
a biodegradable amphiphilic polymer nanomicelle; and
a compound having the structural formula:

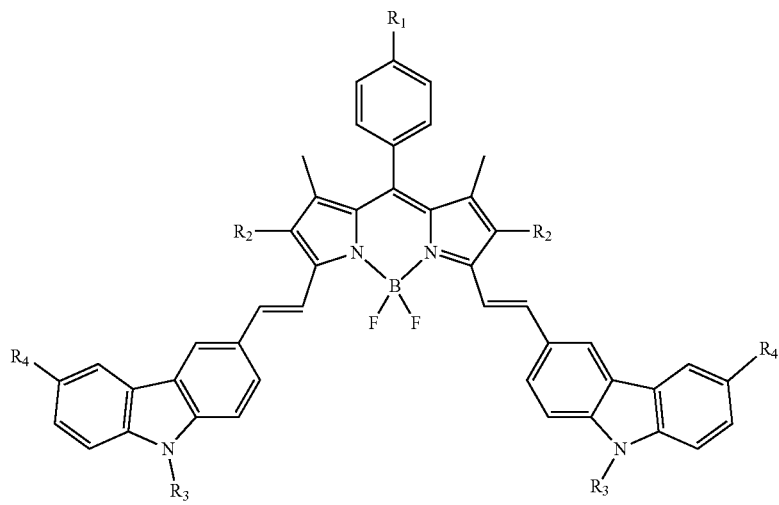

wherein
$R_1$ is selected from the group consisting of H, Br, I, alkynyl, alkyl, alkenyl, azide, PEG, amine, carboxyl acid, and hydroxyl groups;
each $R_2$ is independently selected from the group consisting of Br and I;
each $R_3$ is independently selected from the group consisting of alkynyl, alkyl, alkenyl, azide, PEG, amine, carboxylic acid, and hydroxyl groups;
each $R_4$ is independently selected from the group consisting of H, Br, I, phenyl, and phenylethynyl groups,
or a pharmaceutically acceptable form thereof,
wherein the compound is encapsulated in the biodegradable polymer nanomicelle.

4. The nanoparticulate material of claim 3, wherein the biodegradable amphiphilic polymer nanomicelle is characterized by preferential cellular uptake by cancer or tumor cells.

5. The nanoparticulate material of claim 3, wherein the biodegradable amphiphilic polymer comprises a folic acid moiety.

6. The nanoparticulate material of claim 3, wherein the biodegradable amphiphilic polymer comprises a tumor cell targeting peptide or antibody moiety.

7. The nanoparticulate material of claim 3, wherein the biodegradable amphiphilic polymer comprises a co-polymer having the structural formula:

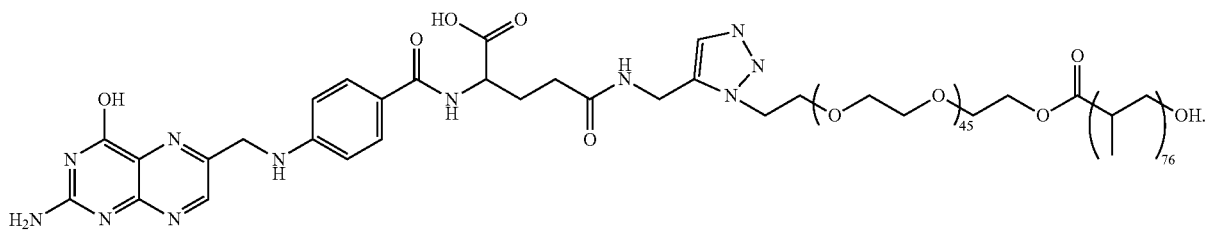

PLA-PEG-FA

8. The nanoparticulate material of claim 3, wherein the biodegradable amphiphilic polymer is
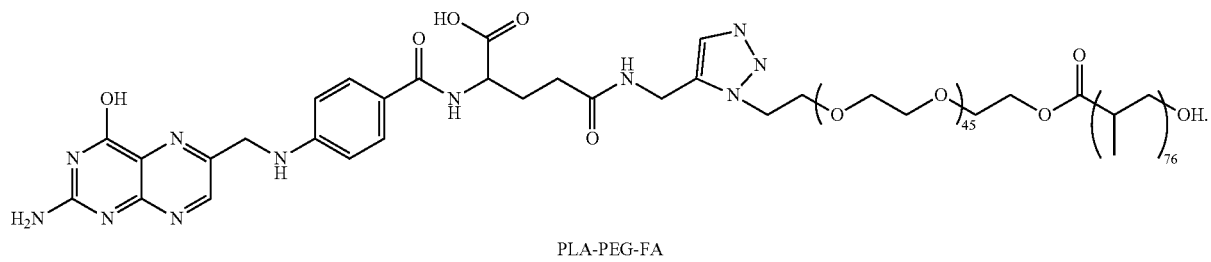
PLA-PEG-FA
9. The nanoparticulate material of claim 3, wherein the compound is
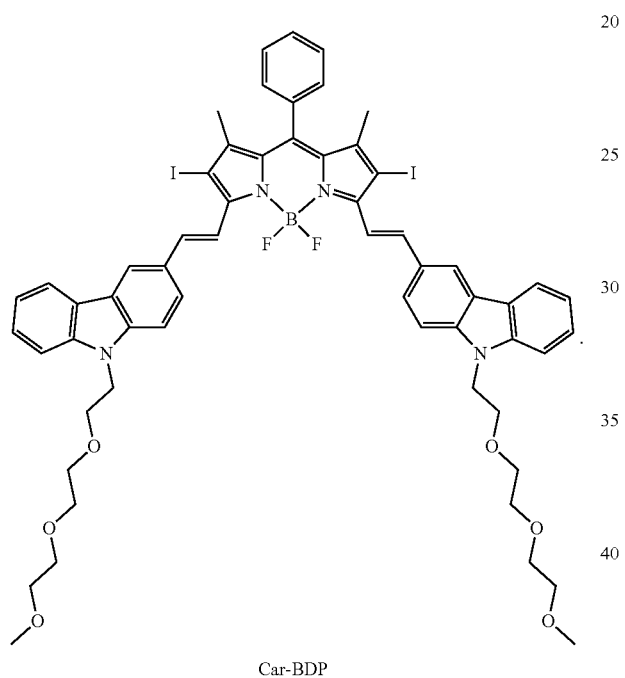
Car-BDP
* * * * *